United States Patent [19]

Kaphammer

[11] Patent Number: 5,608,147
[45] Date of Patent: Mar. 4, 1997

[54] TFDA GENE SELECTABLE MARKERS IN PLANTS AND THE USE THEREOF

[76] Inventor: Bryan J. Kaphammer, 1921 Ravens Crest Dr., Plainsboro, N.J. 08536

[21] Appl. No.: 358,117

[22] Filed: Dec. 15, 1994

Related U.S. Application Data

[63] Continuation-in-part of Ser. No. 179,667, Jan. 11, 1994, abandoned.

[51] Int. Cl.$^6$ .............................. A01H 5/00; A01H 5/10; C12N 15/82
[52] U.S. Cl. .................... 800/205; 800/250; 800/255; 435/172.3; 435/410; 435/419
[58] Field of Search .................... 800/205, 250, 800/255; 435/172.3, 240.4, 240.49, 69.1; 504/214, 215, 247, 353, 189; 47/58, DIG. 9, DIG. 10

[56] References Cited

U.S. PATENT DOCUMENTS

| | | | |
|---|---|---|---|
| 4,459,355 | 7/1984 | Cello et al. | 435/172.3 |
| 4,535,060 | 8/1985 | Comai | 435/172.3 |
| 4,658,082 | 4/1987 | Simpson et al. | 800/1 |
| 4,761,373 | 8/1988 | Anderson et al. | 435/172.3 |
| 4,769,061 | 9/1988 | Comai | 71/86 |
| 4,795,855 | 1/1989 | Fillatti et al. | 800/1 |
| 4,940,835 | 7/1990 | Shah et al. | 800/205 |
| 4,975,374 | 12/1990 | Goodman et al. | 435/172.3 |
| 5,036,007 | 7/1991 | Gupta et al. | 435/240.45 |
| 5,094,945 | 3/1992 | Comai | 435/172.3 |
| 5,145,783 | 9/1992 | Kishore et al. | 435/320.1 |
| 5,149,645 | 9/1992 | Hoekema et al. | 435/172.3 |
| 5,225,341 | 7/1993 | Yoder et al. | 435/172.3 |

FOREIGN PATENT DOCUMENTS

| | | |
|---|---|---|
| 0154204 | 9/1985 | European Pat. Off. . |
| 0492113 | 7/1992 | European Pat. Off. . |
| 0530129 | 3/1993 | European Pat. Off. . |

OTHER PUBLICATIONS

Davis, D. G. and Olson, P.A., "Organogenesis in Leafy Spurge (*Euphorbia esula* L.)," *In Vitro Cell Dev. Biol.* 29P:97–101 (Jul. 1993).

Sullivan, J. and Lagrimini, L. M., "Transformation of *Liquidambar styraciflua* using *Agrobacterium tumefaciens*," *Plant Cell Reports* 12:303–306 (Apr. 1993).

De Block, M., "Factors Influencing the Tissue Culture and the *Agrobacterium tumefaciens*-Mediated Transformation of Hybrid Aspen and Poplar Clones," *Plant Physiol.* 93:1110–1116 (1990).

Fillatti, J. J., et al., "*Agrobacterium* Mediated Transformation and Regeneration of *Populus*," *Mol. Gen. Genet.* 206:192–199 (1987).

Hajela, R. K., et al., "A Simple Transformation System Using Adventitious Shoot Multiplication of Juneberry," *HortScience* 28(4):330–332 (1993).

Barton et al., *Bacillus thuringiensis* delta–Endotoxin Expressed in Transgenic *Nicotiana tabacum* provides Resistance to Lepidopteran Insects, *Plant Physiol.* 85:1103–1109 (1987).

Bayley et al., "Engineering 2,4–D resistance into cotton", *Theor. Appl. Genet.* 83:645–649 (1992).

Bozhkov et al., "A pronounced synergistic effect of abscisic acid and 6–benzyladenine on Norway spruce (*Picea abies* L. Karst) somatic embryo maturation", *Plant Cell Rep.* 11:386–389 (1992).

Brand & Lineberger, "In vitro adventitious shoot formation on mature–phase leaves and petioles of *Liquidambar Styraciflua* L.", *Plant Sci.* 57:173–179 (1988).

Brasileiro et al., "Expression of the mutant *Arabidopsis thaliana* acetolactate synthase gene confers chlorosulfuron resistance to transgenic poplar plants", *Transgenic Res.* 1:133–141 (1992).

Bueno et al., "Plant regeneration through somatic embryogenesis in *Quercus suber*", *Phys. Plant.* 85:30–34 (1992).

Chalupa, V., "Plant regeneration by somatic embryogenesis from cultured immature embryos of oak (*Quercus robur* L.) and linden (*Tilia cordata* Mill.)", *Plant Cell Rep.* 9:398–401 (1990).

Chen & Stomp, "Transformation of *Liquidamber styraciflua* L. (Sweetgum) using *Agrobacterium Tumefaciens*," *Proceedings 21st Southern Forest Tree Improvement Conference*, (Jun. 17–20, 1991), Abstract, p. 315.

Crossway et al., "Integration of foreign DNA following microinjection of tobacco mesophyl protoplasts", *Mol. Gen. Genet.* 202:179–185 (1986).

De Block, M., Genotype–independent leaf disc transformation of potato (*Solanum tuberosum*) using *Agrobacterium tumefaciens*, *Theor. Appl. Genet.* 76:767–774 (1988).

Fasolo et al., "Adventitious shoot formation on excised leaves of in vitro grown shoots of apple cultivars", *Plant Cell, Tissue and Org. Cult.* 16:75–87 (1989).

Gingas & Lineberger, "Asexual embryogenesis and plant regeneration in *Quercus*" *Plant Cell, Tissue and Org. Cult.* 17:191–203 (1989).

Gingas, V. M., "Asexual Embryogenesis and Plant Regeneration from Male Catkins of *Quercus*", *Hort. Sci.* 26:1217–1218 (1991).

Harker et al., "Phenoxyacetic Acid Degradation by the 2,4–Dichlorophenoxyacetic Acid (TFD) Pathway of Plasmid pJP4: Mapping and Characterization of the TFD Regulatory Gene, tfdR", *J. Bacteriol.* 171:314–320 (Jan. 1989).

Hinchee et al., "Production of Transgenic Soybean Plants Using Agrobacterium–Mediated DNA Transfer", *Bio/Technology* 6:915–922 (Aug. 1988).

Hughes, K., Selection of Herbicide Resistance, Handbook of Plant Cell Culture, vol. 1 ( ed. Evans et al.) Mac Millan Publ., NY, pp. 442–460 (1983).

(List continued on next page.)

*Primary Examiner*—Douglas W. Robinson
*Assistant Examiner*—Elizabeth F. McElwain
*Attorney, Agent, or Firm*—Dechert Price & Rhoads

[57] ABSTRACT

The present invention relates, in general, to transgenic plant cells and plants. In particular, the present invention relates to 1) a method of selecting for a transgenic plant cell comprising transforming one or more plant cells with a tfdA gene; 2) a plant cell comprising a tfdA gene wherein said plant cell is free of other foreign marker genes; and 3) a sweetgum plant cell comprising a tfdA gene.

33 Claims, 9 Drawing Sheets

OTHER PUBLICATIONS

Hunt, Hardwood Short Course, "Commercial Hardwood Planting", North Carolina State University, pp. 63–67 (May 15–17, 1973).

James et al., "Factors Affecting High Frequency Plant Regeneration from Apple Leaf Tissues Cultured *in vitro*", *J. Plant Physiol.* 132:148–154 (1988).

Jordan et al., "Glyphosate tolerant flax plants from Agrobacterium mediated gene transfer", *Plant Cell Rep.* 7:281–284 (1988).

Kvaalen & von Arnold, "Effects of various partial pressures of oxygen and carbon dioxide on different stages of somatic embryogenesis in *Picea abies*", *Plant Cell, Tissue and Org. Cult.* 27:49–57 (1991).

Leple et al., "Transgenic poplars: expression of chimeric genes using four different constructs", *Plant Cell Rep.* 11:137–141 (1992).

Lyon et al., "Expression of a bacterial gene in transgenic tobacco plants confers resistance to the herbicide 2,4–dichlorophenoxyacetic acid", *Plant Mol. Biol.* 13:533–540 (1989).

Malac & Heeren, "Hardwood Plantation Management", *Southern J. Appl. Forest.* 3:3–6 (Feb. 1979).

McGranahan et al., "Agrobacterium–mediated transformation of walnut somatic embryos and regeneration of transgenic plants", *Bio/Technology* 6:800–804 (Jul. 1988).

Michler & Bauer, "High frequency somatic embryogenesis from leaf tissues of Populus spp.", *Plant Sci.* 77:111–118 (1991).

Noh & Minocha, "High efficiency shoot regeneration from callus of quaking aspen (*Populus tremuloides* Michx.)", *Plant Cell Rep.* 5:464–467 (1986).

Park & Son, "In vitro organogenesis and somatic embryogenesis from punctured leaf of *Populus nigra X P. maximowiczii*", *Plant Cell, Tissue and Organ Culture* 15:95–105 (1988).

Predieri & Malavasi, "High–frequency shoot regeneration from leaves of the apple rootstock M26 (*Malus pumila* Mill.)", *Plant Cell, Tissue and Organ Culture* 17:133–142 (1989).

Roberts et al., "Synchronous and high frequency germination of interior spruce somatic embryos following partial drying at high relative humidity", *Can. J. Bot.* 68:1086–1090 (1990).

Rowland & Ogden, "Use of a cytokinin conjugate for efficient shoot regeneration from leaf sections of highbush blueberry", *Hort. Sci.* 27:1127–1129 (Oct. 1992).

Stalker et al., "Purification and Properties of a Nitrilase Specific for the Herbicide Bromoxynil and Corresponding Nucleotide Sequence Analysis of the bxn Gene", *J. Biol. Chem.* 263:6310–6314 (May 5, 1988).

Stomp et al., "Extended Host Range of *Agrobacterium tumefaciens* in the Genus Pinus", *Plant Physiology* 92:1226–1232 (1990).

Streber & Willmitzer, "Transgenic tobacco plants expressing a bacterial detoxifying enzyme are resistant to 2,4–D", *Bio/Technology* 7:811–816 (Aug. 1989).

Streber et al., "Analysis, Cloning, and High–Level Expression of 2,4–Dichlorophenoxyacetate Monooxygenase Gene tfdA of Alcaligenes eutrophus JMP134", *J. of Bacteriology* 169:2950–2955 (Jul. 1987).

Thillet et al., "Site–directed Mutagenesis of Mouse Dihydrofolate Reductase", *J. Biol. Chem.* 263:12500–12508 (Sep. 5, 1988).

Tremblay & Tremblay, "Carbohydrate requirements for the development of black spruce (*Picea mariana* (Mill.) B.S.P.) and red spruce (*P. rubens* Sarg.) somatic embryos", *Plant Cell, Tissue, and Org. Cult.* 27:95–103 (1991).

Valobra & James, "In vitro shoot regeneration from leaf discs of *Betula pendula* 'Dalecarlica' EM 85", *Plant Cell, Tissue and Org. Cult.* 21:51–54 (1990).

Wetzstein et al., "Further Characterization of somatic embryogenesis and plantlet regeneration in pecan (*Carya Illinoensis*)", *Plant Sci.* 64:193–201 (1989).

```
GGATCCTGTC TCAGCTGGCG CGCAATGCTC GAACCCGCTG CGATATACAG CCGTTCGTAG      60

TGCAGGTGCT CCACCGTGAT TCCAGGCTCC TGGGGGTAGA AGCGGCCGAC ACCGAGATGG     120

ATGGTGCCGG CACGCAGGGC CTCGATCTGC CGCACCTTGG GCATCAGGGC CAGAGACAGC     180

GTCGCCCCCG GGACCGCCTG CGTGAACGCA TGGAGCAATG CCGGGACGGT CTGGTAGATC     240

GCCGTGCCGA GGTAGCCGAT ATCGAGTTGG CCGATCTCGC CCCGGCTGGC GGCGCGGGAC     300

CGGTCCACGG AAGTCCGACC CAGTTCGAGC ATGCGCCGTG CATCTTCGAG AAACGCGGCC     360

CCGGCGGGCG TGAGCTGCAC GCCGCGCGCG CTGCGCTCGA ACAACAACAC GCCCAGATGC     420

TGTTCGAGCG CGTGAATCTG TCGCGTGACC GGGGGCTGGG AAATATGCAG CCGCCGCGCG     480

GCGGCACCGA CGTTGCCCTC CTCCGCGGCA GCAACGAAAT AGCGAAGCTG TCGAAACTCC     540

ATTCTTCACT CCTGGTGGCT GGCTCCGGCT GCCGGAGAGC CATACCGATC CCGTATCGCT     600
                                                        Xbal
CGCGCTGATG GAAGGTATTA GACCATATGG CCCGGCATTT CTAGACTACC GCCATGATAA     660

AACTCGGCTG CTCTCTCGTC TGCTGGAACA TCTTCAGGCG CGCTGAGCCG TCTTTTTGAA     720

ACAGTCTCTT AGAAAAGGAG CAAAAAAGTG AGC GTC GTC GCA AAT CCC CTT CAT     774
                                 Ser Val Val Ala Asn Pro Leu His
                                  1               5

CCT CTT TTC GCC GCA GGG GTC GAA GAC ATC GAC CTT CGA GAG GCC TTG     822
Pro Leu Phe Ala Ala Gly Val Glu Asp Ile Asp Leu Arg Glu Ala Leu
     10              15               20

GGT TCG ACC GAG GTC CGA GAG ATC GAA CGG CTA ATG GAC GAG AAG TCG     870
Gly Ser Thr Glu Val Arg Glu Ile Glu Arg Leu Met Asp Glu Lys Ser
 25              30              35              40

GTG CTG GTG TTC CGG GGG CAG CCC CTG AGT CAG GAT CAG CAG ATC GCC     918
Val Leu Val Phe Arg Gly Gln Pro Leu Ser Gln Asp Gln Gln Ile Ala
             45              50              55
```

FIG.7A

| | | |
|---|---|---|
| TTC GCG CGC AAT TTC GGG CCA CTC GAA GGC GGT TTC ATC AAG GTC AAT | | 966 |
| Phe Ala Arg Asn Phe Gly Pro Leu Glu Gly Gly Phe Ile Lys Val Asn | | |
|             60               65               70 | | |

```
TTC GCG CGC AAT TTC GGG CCA CTC GAA GGC GGT TTC ATC AAG GTC AAT         966
Phe Ala Arg Asn Phe Gly Pro Leu Glu Gly Gly Phe Ile Lys Val Asn
             60                  65                  70

CAA AGA CCT TCG AGA TTC AAG TAC GCG GAG TTG GCG GAC ATC TCG AAC        1014
Gln Arg Pro Ser Arg Phe Lys Tyr Ala Glu Leu Ala Asp Ile Ser Asn
             75                  80                  85

GTC AGT CTC GAC GGC AAG GTC GCG CAA CGC GAT GCG CGC GAG GTG GTC        1062
Val Ser Leu Asp Gly Lys Val Ala Gln Arg Asp Ala Arg Glu Val Val
             90                  95                 100

GGG AAC TTC GCG AAC CAG CTC TGG CAC AGC GAC AGC TCC TTT CAG CAA        1110
Gly Asn Phe Ala Asn Gln Leu Trp His Ser Asp Ser Ser Phe Gln Gln
105                 110                 115                 120

CCT GCT GCC CGC TAC TCG ATG CTC TCC GCG GTG GTG GTT CCG CCG TCG        1158
Pro Ala Ala Arg Tyr Ser Met Leu Ser Ala Val Val Val Pro Pro Ser
                125                 130                 135

GGC GGC GAC ACC GAG TTC TGC GAC ATG CGT GCG GCA TAC GAC GCG CTG        1206
Gly Gly Asp Thr Glu Phe Cys Asp Met Arg Ala Ala Tyr Asp Ala Leu
                140                 145                 150

CCT CGG GAC CTC CAA TCC GAG TTG GAA GGG CTG CGT GCC GAG CAC TAC        1254
Pro Arg Asp Leu Gln Ser Glu Leu Glu Gly Leu Arg Ala Glu His Tyr
                155                 160                 165

GCA CTG AAC TCC CGC TTC CTG CTC GGC GAC ACC GAC TAT TCG GAA GCG        1302
Ala Leu Asn Ser Arg Phe Leu Leu Gly Asp Thr Asp Tyr Ser Glu Ala
            170                 175                 180

CAA CGC AAT GCC ATG CCG CCG GTC AAC TGG CCG CTG GTT CGA ACC CAC        1350
Gln Arg Asn Ala Met Pro Pro Val Asn Trp Pro Leu Val Arg Thr His
185                 190                 195                 200

GCC GGC TCC GGG CGC AAG TTT CTC TTC ATC GGC GCG CAC GCG AGC CAC        1398
Ala Gly Ser Gly Arg Lys Phe Leu Phe Ile Gly Ala His Ala Ser His
                205                 210                 215
```

FIG.7B

```
GTC GAA GGC CTT CCG GTG GCC GAA GGC CGG ATG CTG CTT GCG GAG CTT    1446
Val Glu Gly Leu Pro Val Ala Glu Gly Arg Met Leu Leu Ala Glu Leu
        220             225                 230
                    EcoRI
CTC GAG CAC GCG ACA CAG CGG GAA TTC GTG TAC CGG CAT CGC TGG AAC    1494
Leu Glu His Ala Thr Gln Arg Glu Phe Val Tyr Arg His Arg Trp Asn
        235                 240                 245

BglII
GTG GGA GAT CTG GTG ATG TGG GAC AAC CGC TGC GTT CTT CAC CGC GGA    1542
Val Gly Asp Leu Val Met Trp Asp Asn Arg Cys Val Leu His Arg Gly
        250                 255                 260

CGC AGG TAC GAC ATC TCG GCC AGG CGT GAG CTG CGC CGG GCG ACC ACC    1590
Arg Arg Tyr Asp Ile Ser Ala Arg Arg Glu Leu Arg Arg Ala Thr Thr
265             270                 275                 280

CTG GAC GAT GCC GTC GTC TAGCGCACGC CATGGCGCAC GCCCTTTTCG           1638
Leu Asp Asp Ala Val Val
                285

CGAAGGCCCC ACAAGATGTA CGCAACCCTG ATCAGCGGCA GCCGTAGCCT GGACGGCGAC  1698

ACCTTGGCGC AGCGCGTCCT TCGAGCGGCG GGCGGCCTGG CGGCATGGGG ATTGAGGCCC  1758

GGTGATGTCG TCGCCATCCT CATGCGCAAT GACTTTCCGG TGCTCGAAAT GACGCTGGCC  1818

GCGAACCGCG CCGGCATCGT TGCGGTGCCT TTGAACTGGC ATGCGAACCG GGACGAGATC  1878

GCCTTCATCC TCGAGGACTG CAAAGCGCGT GTGCTCGTCG CGCACACCGA TCTGCTCAAG  1938

GGCGTTGCAT CCGCGGTGCC CGAGGCCTGC AAGGTGCTGG AAGCCGCGTC GCCGCCCGAG  1998

ATCCGGCAGG CCTATCGGCT GTCCGATGCG TCGTGCACGG CGAACCCGGG CACGGTCGAC  2058
```

FIG.7C

TFDA GENE SELECTABLE MARKERS IN PLANTS AND THE USE THEREOF

CROSS REFERENCE TO RELATED APPLICATIONS

This is a continuation-in-part of U.S. application Ser. No. 08/179,667, filed Jan. 11, 1994, now abandoned, the contents of which are fully incorporated by reference herein.

FIELD OF THE INVENTION

The present invention relates, in general, to transgenic plant cells and plants. In particular, the present invention relates to 1) a method of selecting a transgenic plant cell comprising transforming one or more plant cells with a tfdA gene; 2) a plant cell comprising a tfdA gene wherein said plant cell is free of other foreign marker genes; and 3) a sweetgum plant cell comprising a tfdA gene.

BACKGROUND OF THE INVENTION 2,4-Dichlorophenoxyacetic acid (2,4-D) is a herbicide used to control broadleaf weeds. The gene which encodes the first enzyme in the 2,4-D degradation pathway (FIG. 1) is tfdA. This gene encodes a monoxygenase which catalyzes the conversion of 2,4-D to 2,4-dichlorophenol (DCP). Transgenic tobacco and cotton plants containing the tfdA gene have been shown to have increased tolerance to 2,4-D (Streber et al., *Bio/technology* 7:811–816 (1989) and Bayley et al., *Theor. Appl. Genet.* 83:645–649 (1992), respectively). Until now, attempts to use the tfdA gene as a selectable marker to identify transformed plants have failed. Streber et at., *Bio/technology* 7:811–816 (1989) theorizes that "in a chimeric tissue transformed cells cannot develop into shoots because they are overgrown or otherwise inhibited by untransformed callus that is rapidly developing in the presence of 2,4-D."

SUMMARY OF THE INVENTION

The invention provides a method of selecting for a transgenic plant cell.

The invention further provides a method of selecting for a transgenic plant cell comprising: a) transforming one or more plant cells with a tfdA gene expressible in the plant cell, b) culturing the transformed plant cell with an amount of 2,4-D which inhibits adventitious shoot formation or regeneration from non-transformed plant cells, and c) selecting a plant cell exhibiting growth.

The invention also provides a method of selecting for a transgenic plant comprising: a) transforming one or more plant cells with a tfdA gene expressible in the plant cell, b) culturing the transformed plant cell with an amount of 2,4-D which inhibits adventitious shoot formation or regeneration from non-transformed plant cells, c) selecting a plant cell exhibiting growth, and d) regenerating the plant cell into a plant.

The invention further provides a plant cell comprising a tfdA gene expressible in the plant cell wherein the plant cell is free of other foreign marker genes; a plant regenerated from the plant cell; progeny or a propagule of the plant; and seed produced by the progeny.

The invention further provides a sweetgum plant cell comprising a tfdA gene expressible in the plant cell; a plant regenerated from the sweetgum plant cell; progeny of the plant; a propagule of the plant; and seed produced by the progeny. Herbicide resistance (and more specifically, 2,4-D resistance) in sweetgum would greatly reduce site preparation costs, and possibly make growth of sweetgum (*Liquidamber styraciflua* L.) in plantations economical. Although transgenic tobacco and cotton plants containing the tfdA gene have been shown to have increased tolerance to 2,4-D (Streber et al., *Bio/technology* 7:811–816 (1989) and Bayley et at., *Theor. Appl. Genet.* 83:645–649 (1992), respectively), it was unknown whether tolerance could be conferred into sweetgum. The present invention provides transgenic sweetgum plant cells containing the tfdA gene.

The invention also relates to a method of obtaining and a method of managing a hardwood plantation comprising:

(a) transforming one or more plant cells with a polynucleotide comprising a herbicide resistance gene expressible in said plant cell;

(b) regenerating said plant cell into a plant;

(c) culturing said regenerated plant with an amount of herbicide which will kill non-transformed plants;

(d) selecting a plant exhibiting growth;

(e) propagating said plant to produce many plants;

(f) inducing root formation in said plants;

(g) growing said rooted plants to planting stock size;

(h) planting the planting stock size plants in a sheared, defoliated site, and (i) applying herbicide over the entire site to suppress competition growth until the planting stock can thrive without competition growth control.

The invention also relates to a method of obtaining and a method of managing a hardwood plantation comprising:

(a) transforming one or more plant cells with a polynucleotide comprising a herbicide resistance gene and at least one second gene encoding a foreign selectable marker expressible in said plant cell;

(b) culturing said plant cell with an amount of a chemical which will inhibit adventitious shoot regeneration of plant cells not transformed with the foreign selectable marker gene;

(c) selecting a plant cell exhibiting adventitious shoot regeneration;

(d) regenerating said plant cell into a plant;

(e) propagating said plant to produce many plants;

(f) inducing root formation in said plants;

(g) growing said rooted plants to planting stock size;

(h) planting the planting stock size plants in a sheared, defoliated site, and (i) applying herbicide over the entire site to suppress competition growth until the planting stock can thrive without competition growth control.

The invention also relates to a method for obtaining and a method for managing a hardwood plantation comprising:

(a) transforming one or more plant cells with a polynucleotide comprising a herbicide resistance gene and at least one second gene encoding a foreign selectable marker expressible in said plant cell;

(b) culturing said plant cell with an amount of a chemical which will inhibit adventitious shoot regeneration of plant cells not transformed with the foreign selectable marker gene;

(c) selecting a plant cell exhibiting adventitious shoot regeneration;

(d) regenerating said plant cell into a plant;

(e) culturing said regenerated plant with an amount of herbicide which will kill non-transformed plants;

(f) selecting a plant exhibiting growth;

(g) regenerating said plant cell into a plant;

(h) propagating said plant to produce many plants;

(i) inducing root formation in said plants;

(j) growing said rooted plants to planting stock size;

(k) planting the planting stock size plants in a sheared, defoliated site, and (l) applying herbicide over the entire site to suppress competition growth until the planting stock can thrive without competition growth control.

Preferably, the herbicide resistance gene is the tfdA gene and said herbicide is 2,4-dichlorophenoxyacetic acid, the herbicide resistance gene is the mutant acetohydroxy acid synthase gene from Arabidopis, or the herbicide resistance gene is the 5-enolpyruvylshikimate-3-phosphate synthase gene and said herbicide is glyphosate.

The invention also relates to a method of obtaining and a method of managing a hardwood plantation comprising:

planting stock size plants in a sheared, defoliated site, and applying herbicide over the entire site to suppress competition growth until the planting stock can thrive without competition growth control, wherein said plant is a hardwood comprising a herbicide resistance gene.

The invention also relates to a plantation of hardwood trees comprising hardwood trees comprising a herbicide resistant gene. Preferably, the herbicide resistance gene is the tfdA gene, the mutant acetohydroxy acid synthase gene from Arabidopis, or the 5-enolpyruvylshikimate-3-phosphate synthase gene.

Further objects and advantages of the present invention will be clear from the description that follows.

BRIEF DESCRIPTION OF THE FIGURES

FIG. 7. Sequence of a tfdA gene from FIG. 3 of Streber et al., *J. of Bacteriology* 169:2950–2955 (1987) (SEQ ID NO:1 and SEQ ID NO:2).

DEFINITIONS

Figure 1:
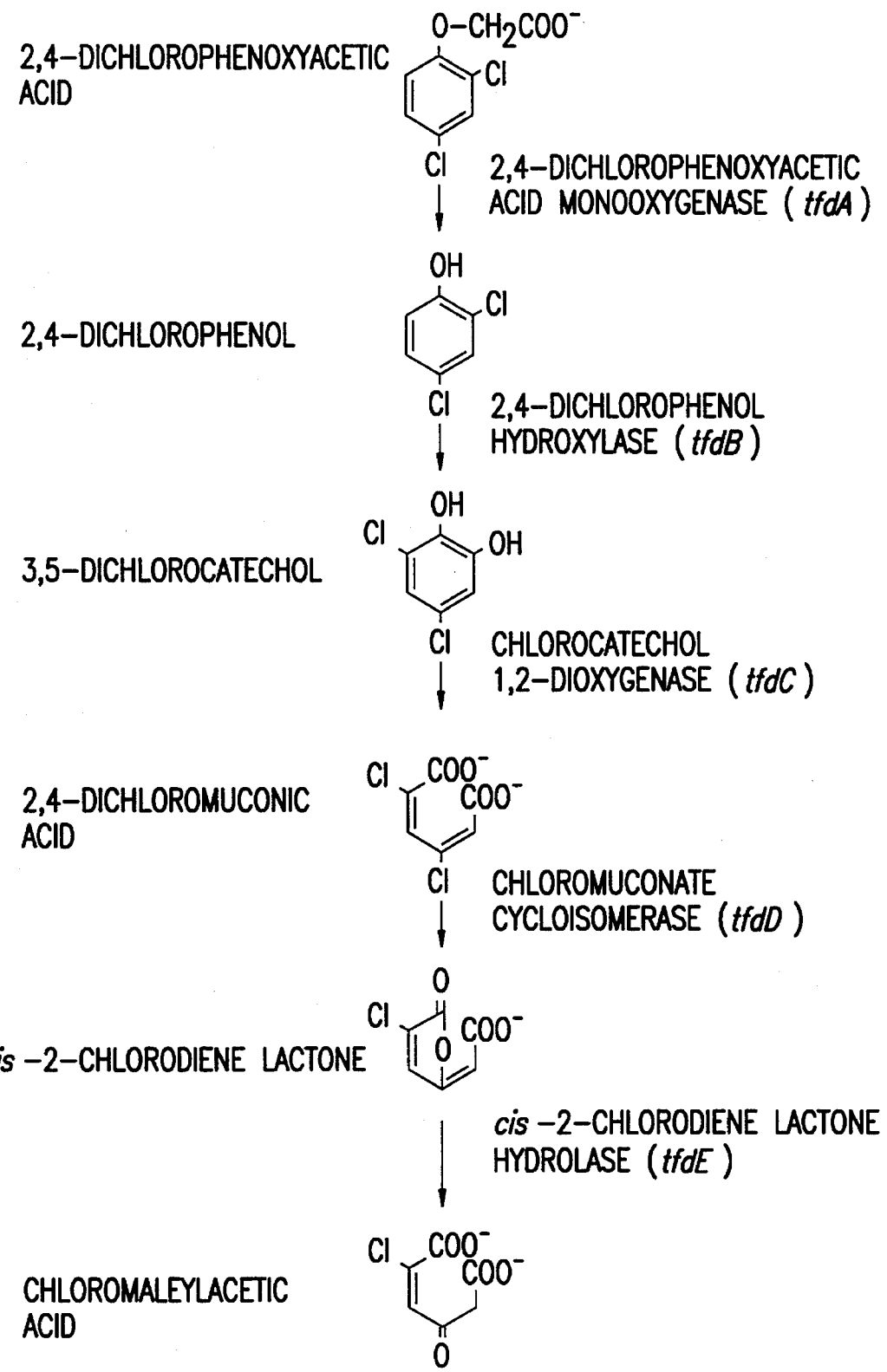
FIG. 1. The 2,4-D degradative pathway. Gene designations are shown in parentheses for each enzyme.

Plant should be understood as referring to a multicellular differentiated organism capable of photosynthesis including angiosperms (monocots and dicots) and gymnosperms.

Plant cell should be understood as referring to the structural and physiological unit of plants. The term "plant cell" refers to any cell which is either part of or derived from a plant. Some examples of cells encompassed by the present invention include differentiated cells that are part of a living plant; differentiated cells in culture; undifferentiated cells in culture; the cells of undifferentiated tissue such as callus or tumors.

Plant cell progeny should be understood as referring to any cell or tissue derived from plant cells including callus; plant parts such as stems, roots, fruits, leaves or flowers; plants; plant seed; pollen; and plant embryos.

Propagules should be understood as referring to any plant material capable of being sexually or asexually propagated, or being propagated in vivo or in vitro. Such propagules preferably consist of the protoplasts, cells, calli, tissues, embryos or seeds of the regenerated plants.

Transgenic plant should be understood as referring to a plant having stably incorporated exogenous DNA in its genetic material. The term also includes exogenous DNA which may be introduced into a cell or protoplast in various forms, including, for example, naked DNA in circular, linear or supercoiled form, DNA contained in nucleosomes or chromosomes or nuclei or parts thereof, DNA complexed or associated with other molecules, DNA enclosed in liposomes, spheroplasts, cells or protoplasts.

DETAILED DESCRIPTION OF THE INVENTION

The present invention relates to a method of selecting for a transgenic plant cell.

In one embodiment, the present invention relates to a method of selecting for a transgenic plant cell comprising: a) transforming one or more plant cells with a tfdA gene expressible in the plant cell, b) culturing the transformed plant cell with an amount of 2,4-D which inhibits formation of adventitious shoots from non-transformed plant cells, and c) selecting a plant cell exhibiting growth.

In another embodiment, the present invention relates to a method of selecting for a transgenic plant comprising: a) transforming one or more plant cells with a tfdA gene expressible in said plant cell, b) culturing said transformed plant cell with an amount of 2,4-D which inhibits formation of adventitious shoots from non-transformed plant cells, c) selecting a plant cell exhibiting growth, and d) regenerating said plant cell into a plant.

All plants which can be transformed are intended to be included within the scope of the invention (preferably, dicotyledonous plants). Such plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Sencia, Salpiglossis, Cucumis, Browalia, Glycine, Lolium, Zea, Triticum, Sorghum, Malus, Apium, and Datura.

Suitable woody dicotyledonous forest tree species (hardwoods) include, for example, species from the genera Acacia, Acer, Actinidia, Albizzia, Alnus, Amelanchier, Atriplex, Betula (Birch), Brachycome, Broussonetia, Camellia, Carya, Castanea (Chestnut), Catalpa, Cinchona, Corylus (Hazelnut), Diospyrus, Eucalyptus, Fagus (Beech), Ficus, Fraxinus (Ash), Gleditsia, Hamamelia, Hedera, Ilex, Kalmia, Liquidambar (Sweetgum), Liriodendron, Moghania, Morus, Paulownia, Populus, Prunus, Quercus (Oak), Rhododendron, Robinia, Salix, Santalum, Sapium, Simmondsia, Tectona, Tupidanthus, Ulmus (Elm), and Vaccinium.

Plant transformation techniques are well known in the art and include direct transformation (which includes, but is not limited to: microinjection (Crossway, *Mol. Gen. Genetics* 202:179–185 (1985)), polyethylene glycol transformation (Krens et al., *Nature* 296:72–74 (1982)), high velocity ballistic penetration (Klein et at., *Nature* 327:70–73 (1987)), fusion of protoplasts with other entities, either minicells, cells, lysosomes, or other fusible lipid-surfaced bodies (Fraley et al., *Proc. Natl. Acad. Sci. USA* 79:1859–1863 (1982)), electroporation (Fromm et al., *Proc. Natl. Acad. Sci. USA* 82:5824 (1985)) and techniques set forth in U.S. Pat. No. 5,231,019)) and *Agrobacterium tumefaciens* mediated transformation (Hoekema et at., *Nature* 303:179 (1983), de Framond et al., *Bio/technology* 1:262 (1983), Fraley et al. WO84/02913, WO84/02919 and WO84/02920, Zambryski et al. EP 116,718, Jordan et al., *Plant Cell Reports* 7:281–284 (1988), Leple et al. *Plant Cell Reports* 11:137–141 (1992), Stomp et at., *Plant Physiol.* 92:1226–1232 (1990), and Knauf et al., *Plasmid* 8:45–54 (1982)). One preferred method of transformation is the leaf disc transformation technique as described by Horsch et at., *Science* 227:1229–1230 (1985).

The above-described transformation techniques can utilize a tfdA gene or fragment thereof expressible in plants. Included within the scope of a tfdA gene are functional derivatives of the tfdA gene, as well as variant, analog, species, allelic and mutational derivatives.

A "fragment" of a molecule is meant to refer to any portion of the amino acid or nucleotide genetic sequence.

A "functional derivative" of a sequence is a molecule that possesses a biological activity (either functional or structural) that is substantially similar to a biological activity of the protein or nucleic acid sequence.

A "variant" of a nucleic acid is meant to refer to a molecule substantially similar in structure and biological activity to the nucleic acid, or to a fragment thereof. Thus, provided that two molecules possess a common activity and may substitute for each other, they are considered variants as that term is used herein even if the nucleotide sequence is not identical.

An "analog" of a protein or genetic sequence is meant to refer to a protein or genetic sequence substantially similar in function to a protein or genetic sequence described herein.

An "allele" is an alternative form of a gene occupying a given locus on the chromosome.

A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

A "species" is a group of actually or potentially interbreeding natural populations. A species variation within a nucleic acid molecule or protein is a change in the nucleic acid or amino acid sequence that occurs among species and may be determined by DNA sequencing of the molecule in question.

The tfdA gene depicted in FIG. 7 (SEQ ID NO:1) can be altered by substitutions, additions or deletions that provide for functionally equivalent molecules. Due to the degeneracy of nucleotide coding sequences, other DNA sequences which encode substantially the same amino acid sequence as depicted in FIG. 7 (SEQ ID NO:2) may be used in the practice of the present invention. These include but are not limited to nucleotide sequences comprising all or portions of the tfdA gene depicted in FIG. 7 (SEQ ID NO:1) which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the tfdA gene and fragments thereof permitted by the genetic code are, therefore, included in this invention.

In addition, the tfdA gene may comprise a nucleotide sequence which results from the addition, deletion or substitution of at least one nucleotide to the 5'-end and/or the 3'-end of the nucleic acid formula shown in SEQ ID NO: 1 or a derivative thereof. Any nucleotide or polynucleotide may be used in this regard, provided that its addition, deletion or substitution does not alter the amino acid sequence of SEQ ID NO:2 which is encoded by the nucleotide sequence. The tfdA gene may, as necessary, have restriction endonuclease recognition sites added to its 5'-end and/or 3'-end.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

The tfdA gene is preferably operably linked to a promoter region functional in plants, a transcription initiation site, and a transcription termination sequence. The particular promoter used in the expression cassette is a noncritical aspect of the invention. Any of a number of promoters which direct transcription in a plant cell is suitable. The promoter can be either constitutive or inducible. Some examples of promoters functional in plants include the nopaline synthase promoter and other promoters derived from native Ti plasmids, viral promoters including the 35S and 19S RNA promoters of cauliflower mosaic virus (Odell et al., *Nature* 313:810–812 (1985)), and numerous plant promoters.

General methods for selecting transgenic plant cells containing a selectable marker are well known and taught, for example, by Herrera-Estrella, L. and Simpson, J., "Foreign Gene Expression in Plants," in *Plant Molecular Biology, A Practical Approach*, C. H. Shaw, ed., IRL Press, Oxford, England (1988), pp. 131–160. For use of the tfdA gene as a selectable marker, the amount of 2,4-D which inhibits adventitious shoot formation from non-transformed plant cells and allows adventitious shoot formation from transformed plant cells can be determined by 1) plating non-transformed cells on media containing various concentrations of 2,4-D and 2) by determining the lowest concentration of 2,4-D which will inhibit adventitious shoot formation by the plant cells. This lowest concentration can then be used to select transformed plant cells. In general, solubilized 2,4-D should be present in an amount ranging from about 0.001 to 5 mg/l culture medium. With regard to the sweetgum plant cells transformed with the tfdA gene, 2,4-D should preferably be present in an amount ranging from about 0.01 to 0.5 mg/l culture medium. A preferred amount of 2,4-D is about 0.01 to 0.2 mg/l culture medium. The amount of 2,4-D to be used for selection of transformed shoot cultures is determined by identifying the minimum concentration of 2,4-D which will inhibit adventitious shoot formation. Expanding leaves from a selected sweetgum clone are surface sterilized and cut into small pieces. The leaf pieces are then placed on WPM 0.1 mg/l NAA, 2.5 mg/l BA containing 2,4-D in concentrations from 0.0 to 5.0 mg/l. The leaf pieces are incubated until the control (no 2,4-D) pieces regenerate shoots. The ideal concentration of 2,4-D for selection of transformants is the lowest concentration of 2,4-D which did not allow regeneration.

In another embodiment, the present invention relates to a plant cell comprising a tfdA gene expressible in the plant cell wherein said plant cell is free of other foreign marker genes (preferably, other foreign selectable marker genes); a plant regenerated from the plant cell; progeny or a propagule of the plant; and seed produced by the progeny.

Plant regeneration techniques are well known in the art and include those set forth in the *Handbook of Plant Cell Culture*, Volumes 1–3, Evans et al., eds., Macmillan Publishing Co., New York, N.Y. (1983, 1984, 1984, respectively); Predieri and Malavasi, *Plant Cell, Tissue, and Organ Culture* 17:133–142 (1989); James, D. J., et at., *J. Plant Physiol.* 132:148–154 (1988); Fasolo, F., et al., *Plant Cell, Tissue, and Organ Culture* 16:75–87 (1989); Valobra and James, *Plant Cell, Tissue, and Organ Culture* 21:51–54 (1990); Srivastava, P. S., et al., *Plant Science* 42:209–214 (1985); Rowland and Ogden, *Hort. Science* 27:1127–1129 (1992); Park and Son, *Plant Cell, Tissue, and Organ Culture* 15:95–105 (1988); Noh and Minocha, *Plant Cell Reports* 5:464–467 (1986); Brand and Lineberger, *Plant Science* 57:173–179 (1988); Bozhkov, P. V., et al., *Plant Cell Reports* 11:386–389 (1992); Kvaalen and von Arnold, *Plant Cell, Tissue, and Organ Culture* 27:49–57 (1991); Tremblay and Tremblay, *Plant Cell Tissue, and Organ Culture* 27:95–103 (1991); Gupta and Pullman, U.S. Pat. No. 5,036,007; Michler and Bauer, *Plant Science* 77:111–118 (1991); Wetzstein, H. Y., et al., *Plant Science* 64:193–201 (1989); McGranahan, G. H., et al., *Bio/Technology* 6:800–804 (1988); Gingas, V. M., *Hort. Science* 26:1217–1218 (1991); Chalupa, V., *Plant Cell Reports* 9:398–401 (1990); Gingas and Lineberger, *Plant Cell, Tissue, and Organ Culture* 17:191–203 (1989); Bureno, M. A., et al., *Phys. Plant.* 85:30–34 (1992); and Roberts, D. R., et al., *Can. J. Bot.* 68:1086–1090 (1990).

The herbicidal resistant plant enables the farmer to plant a herbicidal tolerant crop and then treat the field for weeds without adversely affecting the crop. Further, the herbicidal tolerant plant enables the farmer to grow crops in fields that have been treated with herbicides. These herbicidally treated fields will contain a certain amount of the herbicide in the soil and thus a "herbicide carryover" is seen (U.S. Pat. No. 4,975,374).

Other foreign marker genes (i.e., exogenously introduced genes) typically used include selectable markers such as a neo gene (Potrykus et al., *Mol. Gen. Genet* 199:183–188 (1985)) which codes for kanamycin resistance; a bar gene which codes for bialaphos resistance; a mutant EPSP synthase gene (Hinchee et al., *Bio/technology* 6:915–922 (1988)) which encodes glyphosate resistance; a nitrilase gene which confers resistance to bromoxynil (Stalker et al., *J. Biol. Chem.* 263:6310–6314 (1988)); a mutant acetolactate synthase gene (ALS) which confers imidazolinone or sulphonylurea resistance (EP application number 154,204); a methotrexate resistant DHFR gene (Thillet et al., *J. Biol. Chem.* 263:12500–12508) and screenable markers which include β-glucuronidase (GUS) or an R-locus gene, alone or in combination with a C-locus gene (Ludwig et al., Proc. Natl. Acad. Sci. USA 86:7092 (1989); Paz-Ares et al., *EMBO J.* 6:3553 (1987)).

Plants which contain tfdA gene and no other foreign marker gene are advantageous in that removal of the foreign marker gene, once inserted into the plant, may be impossible without also removing the tfdA gene. Absence of the foreign marker gene is desired so as to minimize the number of foreign genes expressed.

A plasmid which contains only tfdA between the Ti-plasmid boarders can be constructed in several ways. One method is to first partially digest plasmid pUCW200 with EcoRI such that only the EcoRI site on the right side of the NOS-terminator (FIG. 4) is cut. The ends are then made blunt by using standard molecular methods (Maniatis, T. et al., *Molecular Cloning: A Laboratory Manual*, Cold Spring Harbor Laboratory, Cold Spring Harbor, N.Y. (1982)). This linear plasmid is digested with the restriction endonuclease HindIII. The fragment containing tfdA under control of the CaMV 35S promoter is purified by resolving and cutting it out of a low melting temperature agarose gel. This HindIII-EcoRI fragment is ligated into the binary vector pBIN19 (Bevan, M., *Nucleic Acids Research* 12:8711–8721 (1984)) which has first been digested with the restriction endonuclease SstII and the ends made blunt, and then digested with HindIII. The resultant plasmid is then transformed into *E. coli* S17-1 with selection for kanamycin resistance conferred by the kanamycin resistance gene located on plasmid pBIN19, but outside of the left and right boundaries of the Ti-plasmid. This plasmid is then mobilized into *Agrobacterium tumefaciens* LBA 4404 and used to transform the target plant tissue.

In another embodiment, the present invention relates to a sweetgum plant cell comprising a tfdA gene expressible in the plant cell; a plant regenerated from the sweetgum plant cell; progeny of the plant; a propagule of the plant; and seed produced by the progeny.

Historically, establishment of hardwood plantations on cut-over forest land, old agricultural fields, and river bottomland have only been successful when very intensive site preparation has been employed prior to planting (Hunt, *Hardwood Short Course*, North Carolina State University (1973), pp. 63–71). An example of the site preparation methods required is described in "Hardwood Plantation Management" (Malac, B. F. and Heeren, R. D., *Southern Journal of Applied Forestry* 3:3–6 (1979)). Typically, site preparation requires a regiment of shearing, raking, and disking or bedding. The prepared planting site must be clear and level so that directed application of herbicide, for competition control, is possible.

Directed application of herbicide is necessary to avoid killing the hardwood plants. Not only is this intensive site preparation expensive, it also results in site degradation due to soil compaction by heavy machinery and loss of top soil due to raking. This intensive site degradation results in lower yields.

Site preparation requirements will be greatly reduced if hardwoods, which have been genetically engineered to be herbicide resistant, are planted. The herbicide may be applied by aerial spraying. Therefore, the site would not have to be level. This would eliminate the need for raking and disking. Also, the amount of mowing and cultivation required for competition control would be reduced. Less site preparation would have the added benefit of less soil compaction and loss of topsoil, thus, less site degradation and greater yields will result.

Planting of herbicide resistant hardwoods would also have several advantages over planting conventional seedlings or rooted cuttings. These advantages include hand planting, and an opportunity for increasing the number of stems per acre. Hand planting would be possible because, with aerial herbicide application, straight rows are not needed for tractors. If restrictions on spacing required to operate tractors between rows are no longer necessary, more stems per acre could be planted, which would result in increased yields.

Tolerance to the herbicide 2,4-D can be conferred to sweetgum by introduction of a tfdA gene expressible in sweetgum into the sweetgum genome. The tfdA gene may be introduced into sweetgum by the transformation techniques outlined above or more preferably as set forth in Chen, Z. and Stomp, A. (1991) "Transformation of *Liquidamber styraciflua* L. (Sweetgum) using *Agrobacterium Tumefaciens*," In: Proceedings 21$^{st}$ Southern Forest Tree Improvement Conference. Jun. 17–20, 1991 Knoxville, Tenn. A tfdA gene is preferably contained on a plasmid wherein the tfdA gene is operably linked to a promoter region functional in plants, a transcription initiation site, and a transcription termination sequence (examples of which are provided above). In one preferred embodiment, the tfdA gene is linked to a foreign marker gene (described above).

Thus, the invention also relates to a method of managing a hardwood plantation comprising:

(a) transforming one or more plant cells with a polynucleotide comprising a herbicide resistance gene expressible in said plant cell;

(b) regenerating said plant cell into a plant;

(c) culturing said regenerated plant with an amount of herbicide which will kill non-transformed plants;

(d) selecting a plant exhibiting growth;

(e) propagating said plant to produce many plants;

(f) inducing root formation in said plants;

(g) growing said rooted plants to planting stock size;

(h) planting the planting stock size plants in a sheared, defoliated site, and (i) applying herbicide over the entire site to suppress competition growth until the planting stock can thrive without competition growth control.

The invention also relates to a method of managing a hardwood plantation comprising:

(a) transforming one or more plant cells with a polynucleotide comprising a herbicide resistance gene and at least one second gene encoding a foreign selectable marker expressible in said plant cell;

(b) culturing said plant cell with an amount of a chemical which will inhibit adventitious shoot regeneration of plant cells not transformed with the foreign selectable marker gene;

(c) selecting a plant cell exhibiting adventitious shoot regeneration;

(d) regenerating said plant cell into a plant;

(e) propagating said plant to produce many plants;

(f) inducing root formation in said plants;

(g) growing said rooted plants to planting stock size;

(h) planting the planting stock size plants in a sheared, defoliated site, and (i) applying herbicide over the entire site to suppress competition growth until the planting stock can thrive without competition growth control.

The invention also relates to a method for managing a hardwood plantation comprising:

(a) transforming one or more plant cells with a polynucleotide comprising a herbicide resistance gene and at least one second gene encoding a foreign selectable marker expressible in said plant cell;

(b) culturing said plant cell with an amount of a chemical which will inhibit adventitious shoot regeneration of plant cells not transformed with the foreign selectable marker gene;

(c) selecting a plant cell exhibiting adventitious shoot regeneration;

(d) regenerating said plant cell into a plant;

(e) culturing said regenerated plant with an amount of herbicide which will kill non-transformed plants;

(f) selecting a plant exhibiting growth;

(g) regenerating said plant cell into a plant;

(h) propagating said plant to produce many plants;

(i) inducing root formation in said plants;

(j) growing said rooted plants to planting stock size;

(k) planting the planting stock size plants in a sheared, defoliated site, and (l) applying herbicide over the entire site to suppress competition growth until the planting stock can thrive without competition growth control.

The invention also relates to a method of managing a hardwood plantation comprising:

planting stock size plants in a sheared, defoliated site, and applying herbicide over the entire site to suppress competition growth until the planting stock can thrive without competition growth control, wherein said plant is a hardwood comprising a herbicide resistance gene.

The invention also relates to a plantation of hardwood trees comprising hardwood trees comprising a herbicide resistant gene. Preferably, the hardwood trees are sweetgum.

In general, herbicide resistant hardwoods can be constructed by transforming genes which encode proteins which detoxify the herbicide, such as the tfdA gene, or which encode proteins that are not sensitive to the action of the herbicide, such as the mutant acetohydroxy acid synthase gene from Arabidopis (European Patent Application Number 91119254.0, by American Cyanamid Company). Another example of a gene which can confer herbicide resistance is the 5-enolpyruvylshikimate-3-phosphate synthase gene (U.S. Pat. No. 4,940,835, Monsanto Company), which is tolerant to the herbicide glyphosate. Selection for transformation of these genes into the target plant can be done by selecting for the presence of a selectable marker gene, such as the kanamycin resistance gene, which is linked to the herbicide resistance gene. This is done by incubating the target tissue on media containing levels of kanamycin which inhibit regeneration of non-transformed cells. Alternatively, selection can be done by selecting for regeneration in the presence of the herbicide at concentrations which inhibit regeneration of non-transformed cells, or allowing regeneration to take place in the absence of selection and then screening the regenerated plants for presence of the herbicide resistance gene by growing the putative transformants on media containing levels of the herbicide which inhibit growth of non-transformed plants. The preferred method of selecting for transformation of herbicide resistance genes, other than the tfdA gene, is to first select for regeneration in the presence of kanamycin and then screen the regenerated plants by incubating them on media containing levels of the herbicide that are toxic to non-transformed plants.

Plantations are a group of a large number of trees under cultivation. Preferably, nutrients such as triple superphosphate or diammonium phosphate, are added to the soil of the site. See, Davey, C. B., *Hardwood Short Course*, North Carolina State University (1973), pp. 72–75, and "Hardwood Plantation Management" (Malac, B. F. and Heeren, R. D., *Southern Journal of Applied Forestry* 3:3–6 (1979)). In addition, the site may be raked prior to planting the planting stock.

The invention also relates to a method of producing or managing a hardwood plantation, comprising planting stock size plants in a sheared, defoliated site, and applying herbicide over the entire site to suppress competition growth until the planting stock can thrive without competition growth control, wherein the plant is a hardwood comprising a tfdA gene. Preferably, the plant is sweetgum.

The present invention is described in further detail in the following non-limiting examples.

EXAMPLES

The following protocols and experimental details are referenced in the examples that follow.

a. Strain Sources and Growth Conditions.

Figure 2:
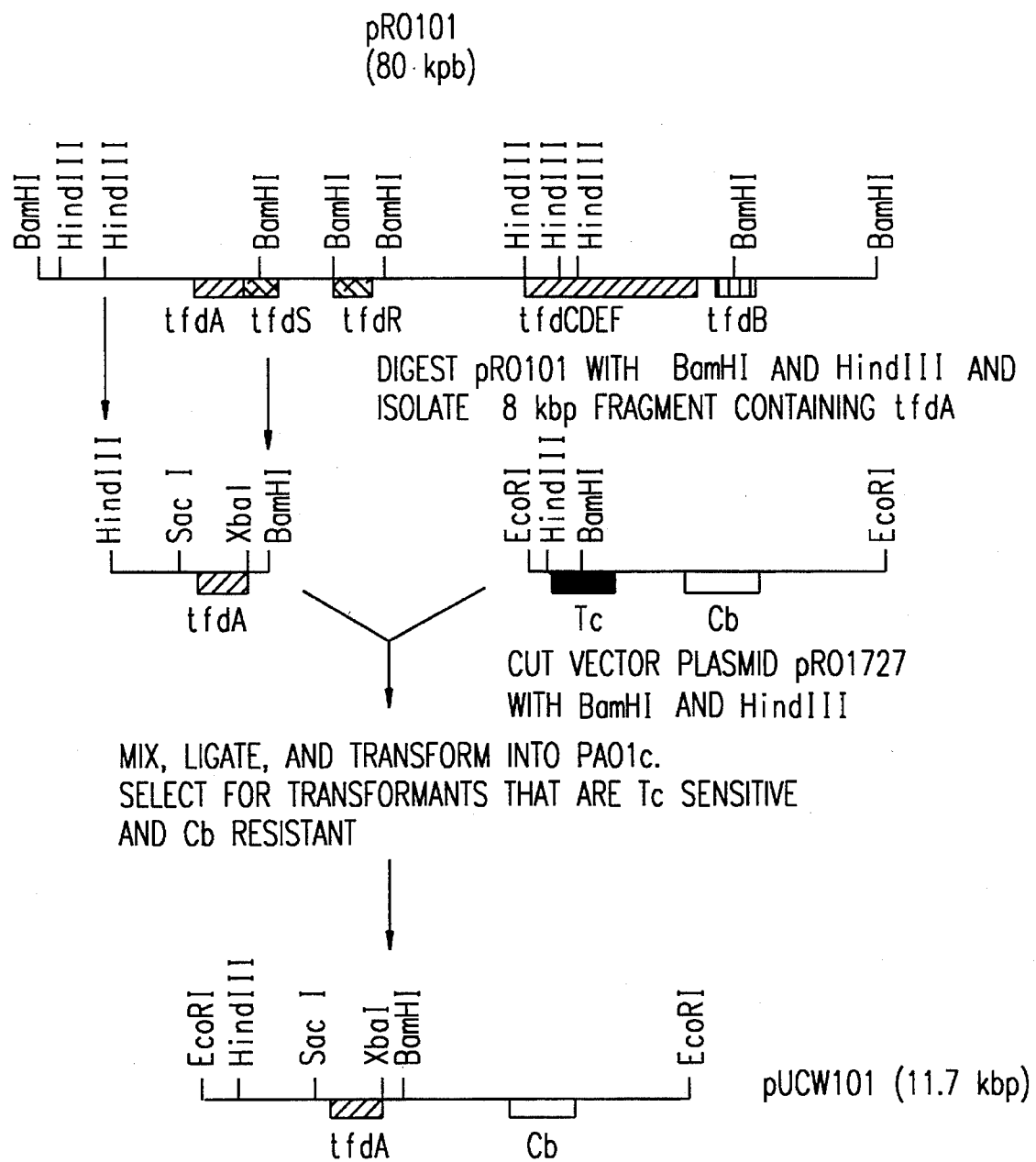
FIG. 2. Construction of pUCW101.
Figure 3:
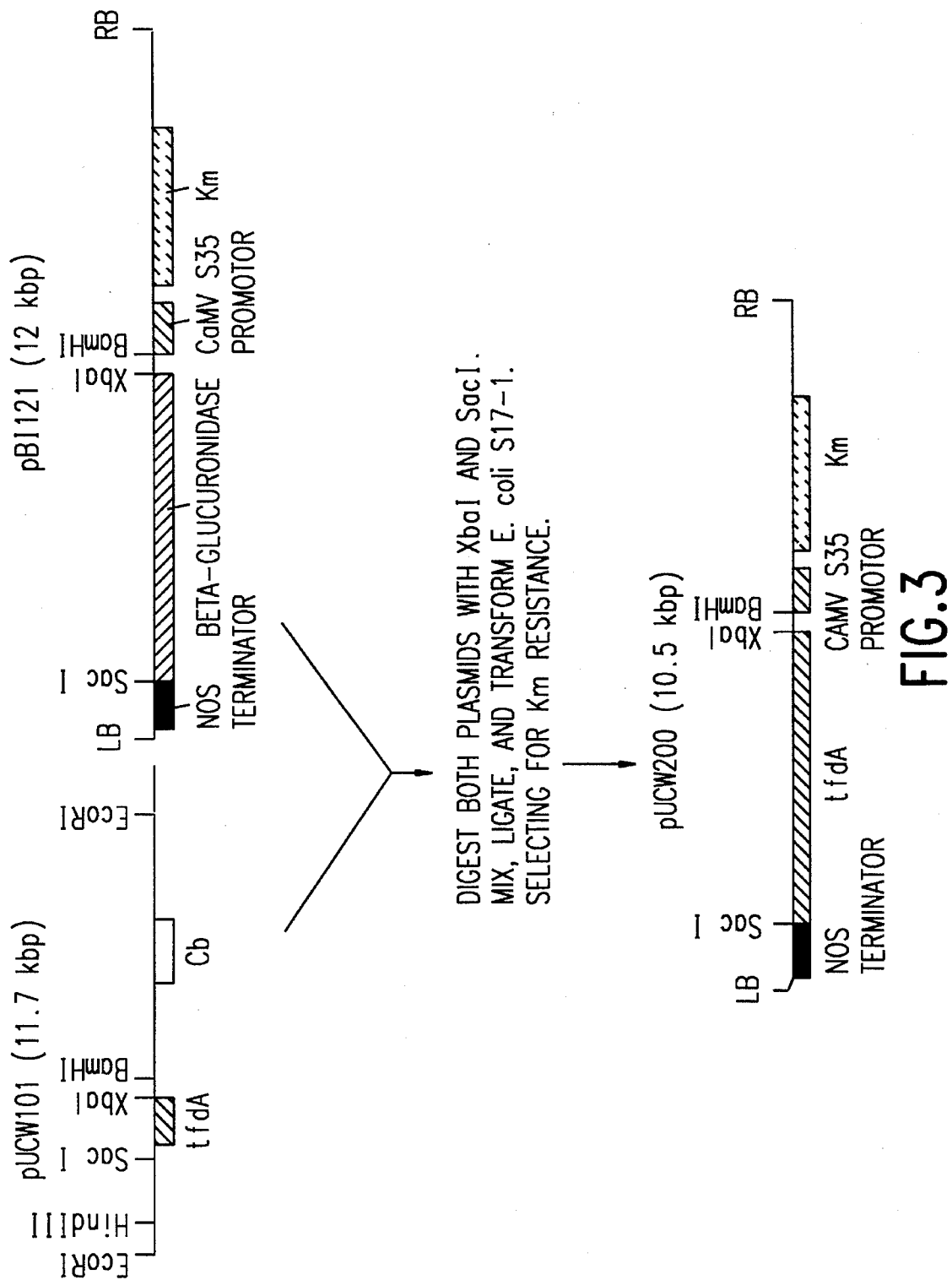
FIG. 3. Construction of pUCW200.

The bacterial strains and plasmids used herein are listed in Table 1, and media formulas are shown in Table 2 and 3. *Pseudomonas aeruginosa* PAO1c containing plasmid pRO101 or plasmid. pRO1727 were grown on TNA plates containing 50 µg/ml tetracycline ($TC^{50}$) at 37° C. *P. aeruginosa* PAO1c (pUCW101; FIG. 2) was grown on TNA containing 500 µg/ml carbenicillin ($Cb^{500}$) at 37° C. *P. putida* PPO300 (pUCW200; FIG. 3), *Agrobacterium tumefaciens* LBA4404 (pUCW200; FIG. 3), *Escherichia coli* HB101 (pBI121, FIG. 4), and *E. coli* S17-1 (pUCW200; FIG. 3) were grown on TNA containing 50 µg/ml kanamycin ($Km^{50}$). The *P. putida* and *A. tumefaciens* strains were grown at 30° C., and the *E. coli* strains were grown at 37° C.

Growth of *P. aeruginosa* PAO1c (pUCW101), *P. putida* PPO300 (pUCW200), and *A. tumefaciens* LBA4404 (pUCW200) for analysis of 2,4-D conversion to DCP was done by inoculating 50 ml of Burk's/CAA media containing 1 mM 2,4-D with a loop of culture from an overnight TNA plate containing the appropriate antibiotic. These liquid cultures were shaken at 30° C. for 4 hours, and then filter sterilized. The sterile filtrate was analyzed by HPLC as described below.

TABLE 1

BACTERIAL STRAINS AND PLASMIDS

| Strain or Plasmid | Relevant Markers[a] | Reference or Source |
|---|---|---|
| *Pseudomonas aeruginosa* PAO1c | Prototroph | Holloway[b] |
| *Pseudomonas putida* PPO300 | Prototroph | ATCC[c] |
| *Escherichia coli* | thi, pro, recA chromo- | Simon[d] |

TABLE 1-continued

BACTERIAL STRAINS AND PLASMIDS

| Strain or Plasmid | Relevant Markers[a] | Reference or Source |
|---|---|---|
| S17-1 | somally integrated RP4 | |
| *Agrobacterium tumefaciens* LBA4404 | Sm | Clontech[c] |
| Plasmids | | |
| pRO1727 | Cb, Tc | Cuskey[f] |
| pRO101 | 2,4-D+, Tc | Harker[g] |
| pBI121 | Km, Gus+ | Clontech[d] |
| pUCW101 | Cb, tfdA+ | FIG. 2 |
| pUCW200 | Km, tfdA+ | FIG. 3 |

[a]: Abbreviations: Sm: streptomycin. Cb: carbenicillin. Tc: tetracycline. Km: kanamycin. Gus: β-glucuronidase.
[b]: Holloway et al., Microbiol. Rev. 43:73–102 (1979).
[c]: ATCC 17514, American Type Culture Collection, Rockville, MD
[d]: Simon, R. et al., Bio/Technology 1:784–791 (1983)
[e]: Clontech Laboratories, Inc., Palo Alto, CA.
[f]: Cuskey et al., J. Bacteriol. 169:2398–2404 (1987).
[g]: Harker et al., J. Bacteriol. 171:314–320 (1989)

TABLE 2

TNA

| | |
|---|---|
| Tryptone | 5.0 g/l |
| Yeast Extract | 2.5 g/l |
| NaCl | 8.5 g/l |
| Glucose | 1.0 g/l |
| Agar | 20.0 g/l |

Autoclave and temper to 50° C. Add antibiotic if required and pour plates.

LB

| | |
|---|---|
| Luria Broth Base | 15.5 g/l |
| Agar | 20.0 g/l |

Autoclave and temper to 50° C. Add antibiotic if required and pour plates.

Burk's Salts*

Stock Solutions:

| | | |
|---|---|---|
| a. | $MgSO_4$-$7H_2O$ | 39.90 g/l |
| b. | $FeSO_4$-$7H_2O$ | 0.01 g/l |
| c. | $NaMoO_4$-$2H_2O$ | 0.05 g/l |
| d. | $(NH_4)_2SO_4$ | 100.00 g/l |
| e. | 1M Potassium Phosphate buffer, pH 7.1 | |

Autoclave stock solution and store at room temperature.
Burk's/CAA

To 1 L of sterile distilled water containing 0.3% casamino acids add:
  5 ml of stock solutions a, b, and c;
  10 ml of stock solutions d and e.
Burk's/succinate plates To 1 L of distilled water containing 0.2% succinate and 2% noble agar, which has been autoclaved and tempered to 50° C. add:
  5 ml of stock solutions a, b, and c;
  10 ml of stock solutions d and e.
Add appropriate antibiotic if desired and pour plates

*Page et al., J. Bacteriol. 125:1080–1087 (1975)

TABLE 3

| WPM 0.1 mg/l NAA, 2.5 mg/l BA[a] | per liter |
|---|---|
| | 100 ml |
| WPM-macro | 10 ml |
| WPM-micro | 10 ml |

TABLE 3-continued

| | |
|---|---|
| WPM-Ca | 10 ml |
| Inositol (10 mg/ml) | 10 ml |
| Chelated Iron[b] | 1 ml |
| WPM Vitamin | 20 ml |
| Sucrose | 2.5 ml |
| NAA (0.1 mg/ml)[c] | |
| BA (0.1 mg/ml)[d] | |
| Bring volume to one liter with distilled $H_2O$, pH to 5.8, add 7 g agar, and autoclave. | |

| WPM-macro | g/l | WPM-micro | g/l |
|---|---|---|---|
| $NH_4NO_3$ | 4.0 | $H_3BO_3$ | 0.67 |
| $K_2SO_4$ | 9.9 | $ZnSO_4$-$7H_2O$ | 0.86 |
| $KH_2PO_4$ | 1.7 | $MnSO_4$-$H_2O$ | 1.69 |
| $MgSO_4$-$7H_2O$ | 3.7 | $Na_2MoO_4$-$2H_2O$ | 0.025 |
| | | $CuSO_4$-$5H_2O$ | 0.025 |

| WPM-Ca | g/100 ml | WPM-Vitamin | g/100 ml |
|---|---|---|---|
| $Ca(NO_3)_2$-$4H_2O$ | 5.56 | Thiamine HCl | 0.1 |
| $CaCl_2$-$H_2O$ | 0.96 | Nicotinic acid | 0.05 |
| | | Pyridoxine HCl | 0.05 |
| | | Glycine | 0.2 |

[a]Lloyd et al., Comb. Proc. Inter. Plant. Prop. Soc. 30:421–427 (1980)
[b]Chelated Iron = $Na_2$ EDTA 3.73 g/l; $FeSO_4$ - $7H_2O$ 2.73 g/l
[c]NAA = Napthaleneacetic acid
[d]BA = Benzylamino purine b. Molecular Biology Methods.

Plasmids were isolated by harvesting the bacterial growth of 10 TNA plates containing the appropriate antibiotic by suspending the growth from each plate in 5 ml of TE buffer (50 mM Tris-HCl, 20 mM EDTA, pH 8.0), pooling the solutions in a 250 ml centrifuge bottle and pelleting the cells by centrifugation at 10,000×g for five minutes. The pellet was resuspended in 20 ml of lysis buffer (50 mM Tris-HCl, pH 8.0, 20 mM EDTA, 50 mM glucose, 2 mg/ml lysozyme), and incubated at room temperature for five minutes. Freshly prepared (40 ml) alkaline-SDS solution (0.2M NaOH, 1% SDS) was added. The cells were lysed by gentle inversion and incubated in an ice water bath for 10 minutes. Potassium acetate (30 ml of a 5M solution) was added, the solution was mixed by gentle inversion and incubated in an ice water bath for 10 minutes. This solution was centrifuged for 10 minutes at 10,000×g, 4° C. The supernatant was decanted to a clean centrifuge bottle and the DNA was precipitated by the addition of two volumes of 95% ethanol and incubation in an ice water bath for 1 hour. The precipitate was collected by centrifugation at 10,000×g for 30 minutes at 4° C. The resulting pellet was resuspended in 10 ml of ice cold TE buffer by slowly passing the mixture through a pipet. After the pellet was resuspended, 5 ml of 7.5M ammonium acetate was mixed in by gentle inversion. This solution was incubated in an ice water bath for 20 minutes and then centrifuged for 10 minutes at 10,000×g and 4° C. The supernatant was decanted to a 50 ml centrifuge tube and 0.313 volumes of 42% polyethylene glycol (MW 6000–8000) was mixed in by gentle inversion. The DNA was allowed to precipitate from 4 hours to overnight at 4° C. The DNA was collected by centrifugation at 10,000×g for 10 minutes at 4° C. The pellet was resuspended in 8 ml of ice cold TE buffer and then added to 8 g of cesium chloride. After the cesium chloride was in solution, 0.6 ml of a 10 mg/ml solution (in distilled water) of ethidium bromide was added. The solution was centrifuged in an ultracentrifuge at 40,000 rpm for 42 hours at 20° C., using a Ti50 rotor. The plasmid band from this cesium chloride-ethidium bromide gradient was drawn off using a pasteur pipet. The ethidium bromide was removed by several extractions with water saturated n-butanol and then dialyzed for 24 hours, with two buffer changes, in a TE buffer solution. The purified DNA was stored at −20° C.

Routine analysis of strains for the desired plasmid was done by mini-prep. A loop of culture taken from a TNA antibiotic plate was suspended in 100 µl of lysis buffer by vortexing. After 5 minutes of incubation at room temperature, 200 µl of alkaline-SDS solution was mixed in by gentle inversion and the lysed cells were incubated in an ice water bath for 10 minutes. Potassium acetate (150 µl of a 5M solution) was mixed in by gentle inversion and incubation in the ice water bath was continued for 5 minutes. The lysate was cleared by microfugation at 4° C. for 5 minutes, and the supernatant was decanted to a fresh tube. The DNA was precipitated by adding 1 ml of 95% ethanol and incubating the mixture at −70° C. for 30 minutes, followed by microfugation for 30 minutes. The pellet was resuspended in 100 µl of ice cold, sterile distilled water, and 50 µl of 7.5M ammonium acetate was mixed in by gentle inversion of the tube. This mixture was incubated in an ice water bath for 10 minutes, microfuged for 2 minutes, and the supernatant was decanted to a fresh tube. The DNA was precipitated by addition of 300 µl of 95% ethanol, incubation at −70° C. for 30 minutes, and microfugation for 30 minutes. The DNA pellet was dried by vacuum desiccation for 10 minutes, and resuspended in 40 µl of TE buffer. Analysis was done by agarose gel electrophoresis as described below.

Restriction endonuclease digestion was done by incubating the purified plasmid DNA in the appropriate Boehringer Mannheim buffer with 1–2 µl of the required Boehringer Mannheim restriction endonuclease, at 37° C. for 1 hour. The reaction was inactivated by incubation at 70° C. for 10 minutes, followed by incubation in an ice water bath for 10 minutes.

DNA ligation was performed by mixing the two restriction endonuclease digested DNA fragments to be ligated, adding 1/10 volume 7.5M ammonium acetate, and two volumes of 95% ethanol. The DNA in this solution was precipitated by incubation at −70° C. for 30 minutes and then centrifugation for 30 minutes at 4° C. in the microfuge. The pellet was resuspended in 100 µl of ice cold sterile distilled water by vortexing for 15 seconds. The resuspended DNA was reprecipitated by the ammonium acetate-ethanol method described above. After the second precipitation, the DNA pellet was dried by vacuum desiccation for 10 minutes, resuspended in 16 µl of ice cold sterile distilled water and 4 µl of 5X Gibco-BRL ligase buffer was added. Gibco-BRL T4 ligase was added to 1 Wiess unit. The ligation mixture was incubated at room temperature for 2 hours, and stopped by addition of 30 µl of ice cold, sterile distilled water.

Analysis of plasmids and DNA fragments was done by agarose gel electrophoresis. The gel is made by adding agarose to a final concentration of 0.7% in TAE buffer (40 mM Tris-acetate, 0.1 mM EDTA). A 15 cm$^2$ gel had a total volume of 100 ml and a mini-gel had a total volume of 25 ml. The agarose buffer solution was melted in the microwave, tempered to 50° C. and then poured into the gel mold and allowed to solidify for 20 minutes. The cast gel was then placed in the gel box, and submerged in TAE buffer. The DNA was loaded into the wells, and electrophoresed for 2.5 hours at 100 volts when 15 cm$^2$ gels were run, and 45 minutes at 130 volts when mini-gels were run. The DNA was visualized by staining the gel in 300 ml of water containing 40 µl of 10 mg/ml ethidium bromide solution for 20 minutes, and then exposing the gel to UV light at 305 nm. The gel was photographed using a Fisher Brand photodocumentation system and Polaroid 660 film.

Low melting temperature agarose gels were run as described above, except the amount of low melting agarose was 1% and the gels were run at 4° C. The DNA was visualized by ethidium bromide staining, and the desired fragment was cut out of the gel. The excised fragment was eluted from the gel matrix by adding 100 µl of TE buffer and incubating at 70° C. for 10 minutes. An equal volume of TE saturated phenol was added and mixed in by gentle inversion. The phases were separated by microfuging the sample for 3 minutes at 4° C. The top (aqueous) layer was collected, and the phenol layer was extracted twice more with an equal volume of TE buffer. The aqueous phases were pooled and extracted once with a 1:1 mixture of phenol:chloroform and once with chloroform. The DNA was precipitated by adding 1/10 volume of 7.5M ammonium acetate, 2 volumes of 95% ethanol, incubation at −70° C. for 30 minutes, and microfugation for 30 minutes. The pellet was vacuum dried for 10 minutes and then resuspended in 100 µl of TE buffer.

c. Transformation and Conjugation Methods.

Transformation of *P. aeruginosa* PAO1c was as described by Mercer et al. (Mercer, A. A. and Loutit, J. S., *J. Bacteriol.* 140:37–42 (1979)). *E. coli* S17-1 was transformed as described by Maniatis et al. (Maniatis, T. et al., Molecular cloning: a laboratory manual, Cold Spring Harbor Laboratory, Cold Spring Harbor, N.Y. (1982).

Transfer of plasmid pUCW200 from *E. coli* S17-1 to *P. putida* PPO300 or *A. tumefaciens* LBA4404 by conjugation was done by growing the strains at 30° C. in LB media or LB containing 50 µg/ml kanamycin (*E. coli* S17-1) and then mixing equal volumes of each culture, filtering the mixture through a sterile 0.22 µm filter and placing the filter on an LB plate. The plates were incubated overnight at 30° C., followed by washing the filter with 5 ml of sterile distilled water and plating dilutions of the cell suspension on Burk's salts containing 0.2% succinate and 50 µg/ml kanamycin. These plates were incubated at 30° C. for 48 hours and the transconjugates were purified by restreaking to identical media.

d. HPLC Analysis for 2,4-D and DCP.

HPLC analysis was done using a Supelco C8 column, a mobile phase of 70:30 methanol:water at 1 ml/min., and detection at 280 nm of a 20 µl injection. Peaks were identified by comparison of retention times to those of known standards.

Example 1

Construction of Plasmid pUCW101.

To construct pUCW101 (FIG. 2), plasmid pRO101, which encodes all the enzymes for the degradation of 2,4-D to chloromaleylacetic acid, was digested with restriction endonucleases BamHI and HindIII. The DNA fragment containing the tfdA gene was isolated from a low melting temperature agarose gel and ligated into vector plasmid pRO1727 which had been digested with the same restriction endonucleases. The ligated DNA was transformed into *P. aeruginosa* PAO1c and transformants which contained the desired insert were selected by plating for growth on TNA Cb$^{500}$, followed by replica plating to DNA Tc$^{50}$ and TNA Cb$^{500}$. Strains with the correct phenotype of Tc sensitivity (due to insertional inactivation) and Cb resistance were characterized further by isolation of the plasmid DNA and digestion with BamHI and HindIII. The digested plasmid DNA was analyzed by agarose gel electrophoresis to confirm that the desired fragment had been cloned. This plasmid was designated pUCW101, FIG. 2.

Expression of tfdA on plasmid pUCW101 in *P. aeruginosa* PAO1c was confirmed by growth of this strain in the presence of 2,4-D and detection of DCP by HPLC.

Example 2

Construction of Plasmid pUCW200.

The *A. tumefaciens* binary vector pBI121 (Clontech Laboratories, Inc., Palo Alto, Calif.; shown in FIG. 4) was used to transfer and stably express tfdA in sweetgum. pBI121 contains the transcriptional and translational start sequences of the cauliflower mosaic virus 35S promotor, and the transcriptional termination and polyadenylation sites and the translational stop codons from the nopaline synthase (NOS) gene. pBI121 also contains left and right T-DNA borders (LB and RB) which are sequences used for transformation of a plant cell (See Zambryski et al., *Cell* 56:193–201 (1989) and Zambryski et al., *Annu. Rev. Plant Physiol. & Plant Mol. Biol.* 43:465–490 (1992)). DNA between these boundaries will be inserted and then replicated with the plant's chromosomal DNA.

Subcloning tfdA into plasmid pBI121 creating plasmid pUCW200 was accomplished as diagramed in FIG. 3. Plasmid pUCW101 was digested with restriction endonucleases XbaI and SacI. The DNA fragment containing the tfdA gene was isolated from a low melting temperature agarose gel and ligated into plasmid pBI121 which had been cut with the same enzymes. This mixture was transformed into *E. coli* S 17-1, and transformants were selected for growth on LB Km$^{50}$ at 37° C. Transformants were picked, grown overnight on identical media and analyzed for inserts by mini-prep analysis. One strain which seemed to contain the proper insert was further characterized by purifying the plasmid DNA as described above and confirming the insert by digestion with XbaI and SacI. This plasmid was designated pUCW200, FIG. 3. It contains the tfdA gene in the Agrobacterium binary vector pBI121.

Expression of tfdA on plasmid pUCW200 was tested by first transferring the plasmid from *E. coli* S17-1 into *P. putida* PPO300 by conjugation, and then growing *P. putida* (pUCW200) in the presence of 2,4-D and detecting DCP by HPLC.

Plasmid pUCW200 was mobilized from *E. coli* S 17-1 to *A. tumefaciens* LBA4404 as described above. The presence of plasmid pUCW200 in *A. tumefaciens* LBA4404 was confirmed by mini-prep analysis. Expression of tfdA in this strain was confirmed by growing *A. tumefaciens* LBA4404 (pUCW200) in the presence of 2,4-D and demonstrating the accumulation of DCP in the media by HPLC.

Example 3

2,4-D Toxicity to Sweetgum.

The effect of 2,4-D on adventitious shoot regeneration from sweetgum leaf pieces was examined. The results of the 2,4-D toxicity test are shown in Table 4. Two 2,4-D concentrations were tested with two sweetgum clones. The highest concentration (1.0 mg/L) resulted in leaf pieces which formed callus tissue, while the lower concentration (0.1 mg/L) resulted in callus and root formation on the leaf pieces. No shoots were observed on leaf pieces at either concentration. Thus, adventitious shoot formation in the presence of 0.1 mg/L 2,4-D may be used as an indicator of 2,4-D resistance.

TABLE 4

2,4-D TOXICITY TO SWEETGUM

| Sweetgum Clone | (2,4-D) mg/L | # roots/leaf piece | Callus |
|---|---|---|---|
| 2040 | 1.0 | 0.00 | yes |
| 2040 | 0.1 | 6.53 | yes |
| 2071 | 1.0 | 0.00 | yes |
| 2071 | 0.1 | 3.94 | yes |

Example 4

Transformation of Sweetgum with pBI121.

*Agrobacterium tumefaciens*-mediated transformation was used to transform sweetgum. *Agrobacterium tumefaciens* LB4404 has the ability to transfer vector plasmid pBI121 (FIG. 4) into a plant cell. Once inside the plant cell, DNA between the right (RB) and left (LB) borders integrates (randomly) into the plant's chromosome. It is then replicated as if it were a part of the genome of the plant, and thus, when this cell divides and differentiates into a shoot, all the cells of this adventitious shoot contain the gene transformed into the original target cell.

The sweetgum transformation method used is outlined below:

1. The expanding leaves from a known sweetgum clone were surface sterilize by first rinsing them with soapy water and then stirring them in 10% bleach solution (in sterile water) for 10 minutes, followed by three rinses (for 2 minutes each) with sterile distilled water.

2. Each leaf was aseptically cut into small (5 to 10 mm) pieces. Some of the pieces were placed on WPM 0.1/2.5 (Table 2). These pieces acted as the regeneration control.

3. *Agrobacterium tumefaciens* LB4404, containing plasmid pBI121, was grown overnight at 30° C. in 50 ml of LB containing 50 mg/L kanamycin. The next morning this culture was inoculated into 500 ml of the identical media, and the strain was grown for 4 hours at 30° C. The cells were harvested by centrifugation (5 min at 10,000×g), washed once with LB, and finally, resuspended in 100 ml of fresh LB.

4. The leaf pieces were co-cultivated with Agrobacterium for 30 minutes at room temperature. They were then blotted dry on sterile Whatman No. 3 filter paper and placed on WPM 0.1/2.5. The plates were sealed with parafilm and incubated in the growth chamber.

5. After three days, the leaf pieces were transferred to WPM 0.1/2.5 which contained 500 mg/L carbenicillin ($Cb^{500}$). Carbenicillin, an antibiotic, was used to kill the residual Agrobacterium.

Figure 4:
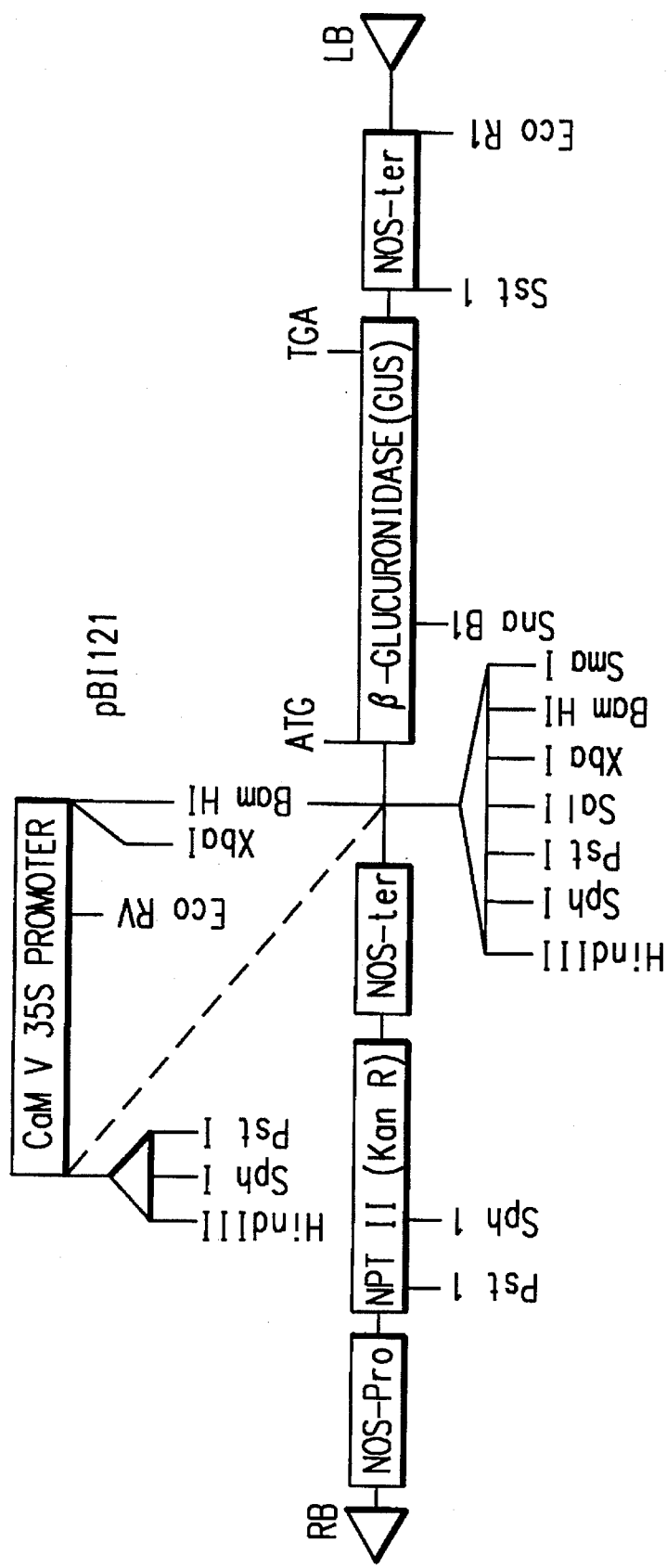
FIG. 4. Construction of pBI121.

6. After two weeks, the non-control leaf pieces were transferred to selective media. In this case, that was WPM 0.1/2.5 $Cb^{500}$, kanamycin 75 mg/L ($Km^{75}$). Plasmid pBI121 contains the kanamycin resistance gene, NPTII (FIG. 4). Sweetgum is sensitive to kanamycin at 75 mg/L, and will not regenerate in its presence. Therefore, adventitious shoots formed in the presence of kanamycin may contain the resistance gene.

7. Shoots, regenerated under selective pressure, were excised from the leaf piece and transferred to WPM 0.01/2.0 $Cb^{500}$, $Km^{75}$.

Twenty-four putatively transformed sweet gum shoots that grew on WPM 0.01 mg/l NAA, 2.0 mg/l BA, $Cb^{500}$, $Km^{75}$ were obtained in an experiment following the above-described transformation protocol.

Example 5

Transformation of Sweetgum with pUCW200.

A sweetgum transformation experiment was performed with *Agrobacterium tumefaciens* LBA4404, containing plasmid pUCW200, as described above, except the selection (at step 6) was altered. Half of the leaf pieces were placed on WPM 0.1/2.5 $Cb^{500}$ with 0.1 mg/L 2,4-D, and the other half were placed on the normal WPM 0.1/2.5 $Cb^{500}$, $Km^{75}$. The results of this selection are shown in Table 5.

TABLE 5

EFFECT OF 2,4-D SELECTION ON SWEETGUM TRANSFORMATION FREQUENCY

| Clone | Selection Media | # shoots/# leaf pieces | Ratio (shoots/ leaf piece) |
|---|---|---|---|
| 2027 (control) | Cb, control | 73/18 | 4.06 |
| 2027 (pUCW200) | Cb, 2,4-D | 38/72 | 0.53 |
| 2027 (pUCW200) | Cb, Km | 3/85 | 0.04 |
| 2040 (control) | Cb, control | 85/30 | 2.83 |
| 2040 (pUCW200) | Cb, 2,4-D | 77/66 | 1.17 |
| 2040 (pUCW200) | Cb, Km | 16/49 | 0.33 |

Abbreviations: Cb = carbenicillin. Km = kanamycin.

Example 6

ELISA Analysis of Transformed Sweetgum Clones.

An analytical method used to confirm the transfer of selected genes into sweetgum clones is an enzyme linked immunosorbant assay (ELISA) for the detection of the NPTII protein encoded by the kanamycin resistance gene on plasmid PBI121. (NPTTII ELISA Kit, Prime Report 3(2):3 (1991)). Plant tissue (from 100 to 800 mg fresh weight) is placed in 3 ml of extraction buffer (0.25M Tris-HCl, pH 7.8, 0.1 mM phenylmethylsulfonyl fluoride) and homogenized using a Tekmar Tissuizer, model TR-10 (equipped with a microprobe), for the two pulses of 30 seconds each. An additional 2 ml of extraction buffer is added and the cellular debris is removed by ultracentrifugation at 50,000 RPM for 20 minutes at 4° C. The supernatant is collected and 4 volumes of ice cold acetone are added, followed by incubation at −20° C. for four hours, or up to overnight. The precipitated proteins are collected by centrifugation at 4° C., 10,000 RPM for 20 minutes. The pellet is resuspended in 1 ml of extract buffer. This sample is used in the NPT-II ELISA kit purchased from 5 Prime - 3 Prime, Inc., Boulder, Colo.

The ELISA method involves using an antibody specific for the kanamycin resistance protein (neomycin phosphotransferase, NPT-II) to detect this protein in the cytoplasmic fraction of putative sweetgum transformants. The presence of this protein is an indication of transformation because the gene encoding it is located on the *Agrobacterium tumefaciens* LBA4404 vector plasmid pBI121. This plasmid is transferred into the target plant cell by *A. tumefaciens* LBA4404 where it integrates into the plant's genome and expresses its genes. Since the genes on this plasmid are physically linked, the presence of one of the gene products is evidence of the presence of the other genes located on the plasmid. For example, presence of the NPT-II protein in plant extracts transformed with plasmid pUCW200, the 2,4-D resistance plasmid, which also contains the kanamycin resistance gene, is positive evidence for the presence of the 2,4-D resistance gene.

Example 7

ELISA Results of Sweetgum/pBI121 Constructions.

Figure 5:
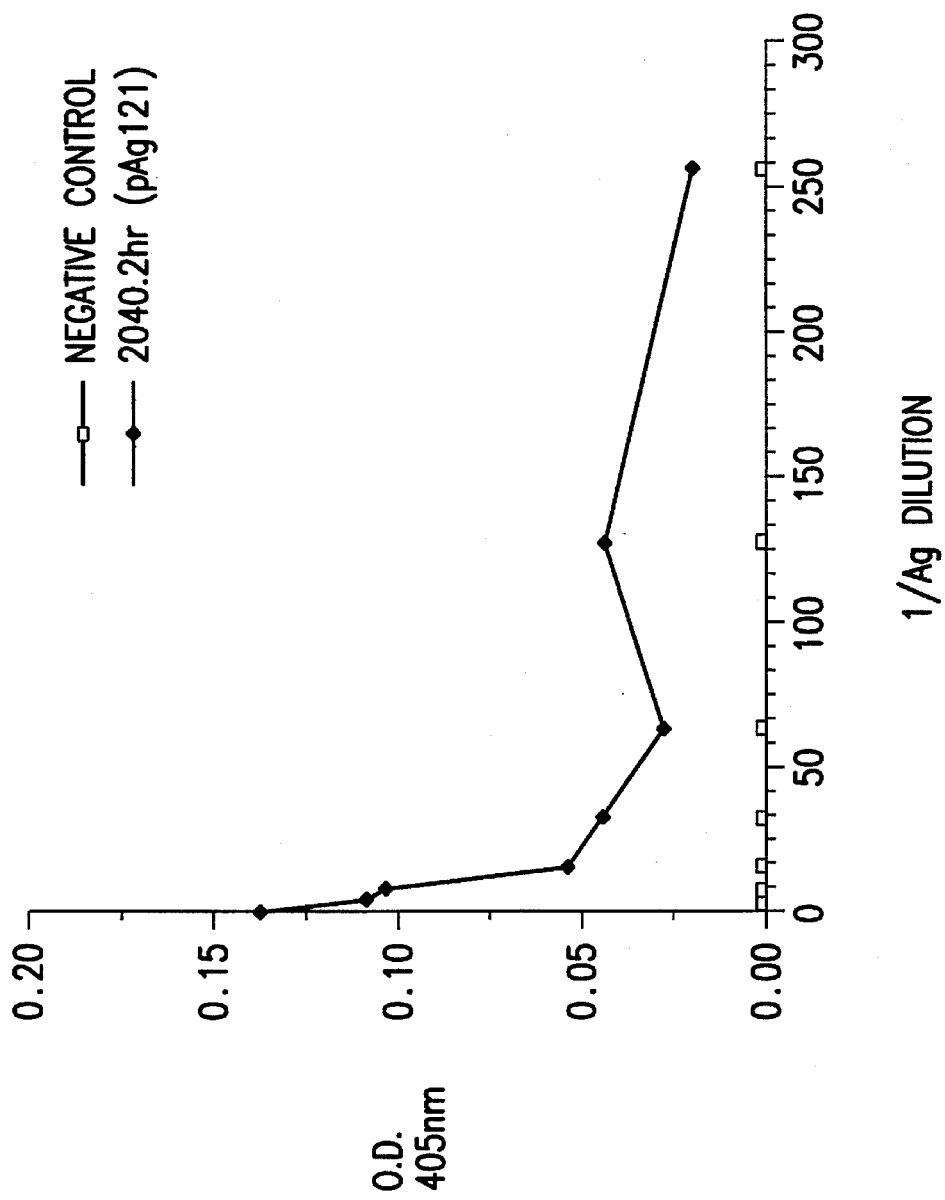
FIG. 5. ELISA of sweetgum 2040 selected on kanamycin.

Of the above-described 24 shoots obtained from the pBI121 transformation experiment, only 15 survived further selection on kanamycin. These 15 were tested for the presence of NPT-II by ELISA. Only one clone, 2040.2hr (pAG121), gave a positive result in this assay (FIG. 5). The ELISA results of FIG. 5 are shown as the $A_{405}$ nm vs the reciprocal of the antigen dilution. The antigen in this case is the plant cell extract, which is serially diluted down the microtiter plate. A positive reaction is one in which the sample shows a decrease in absorbance in correlation to dilution of the antigen. The minimum absorbance value considered to be positive, after correction for background, is an $O.D._{405}$ of 0.1. The transformation frequency in these experiments was 6.7%.

Example 8

ELISA Results of Sweetgum/pUCW200 Transformation.

Figure 6:
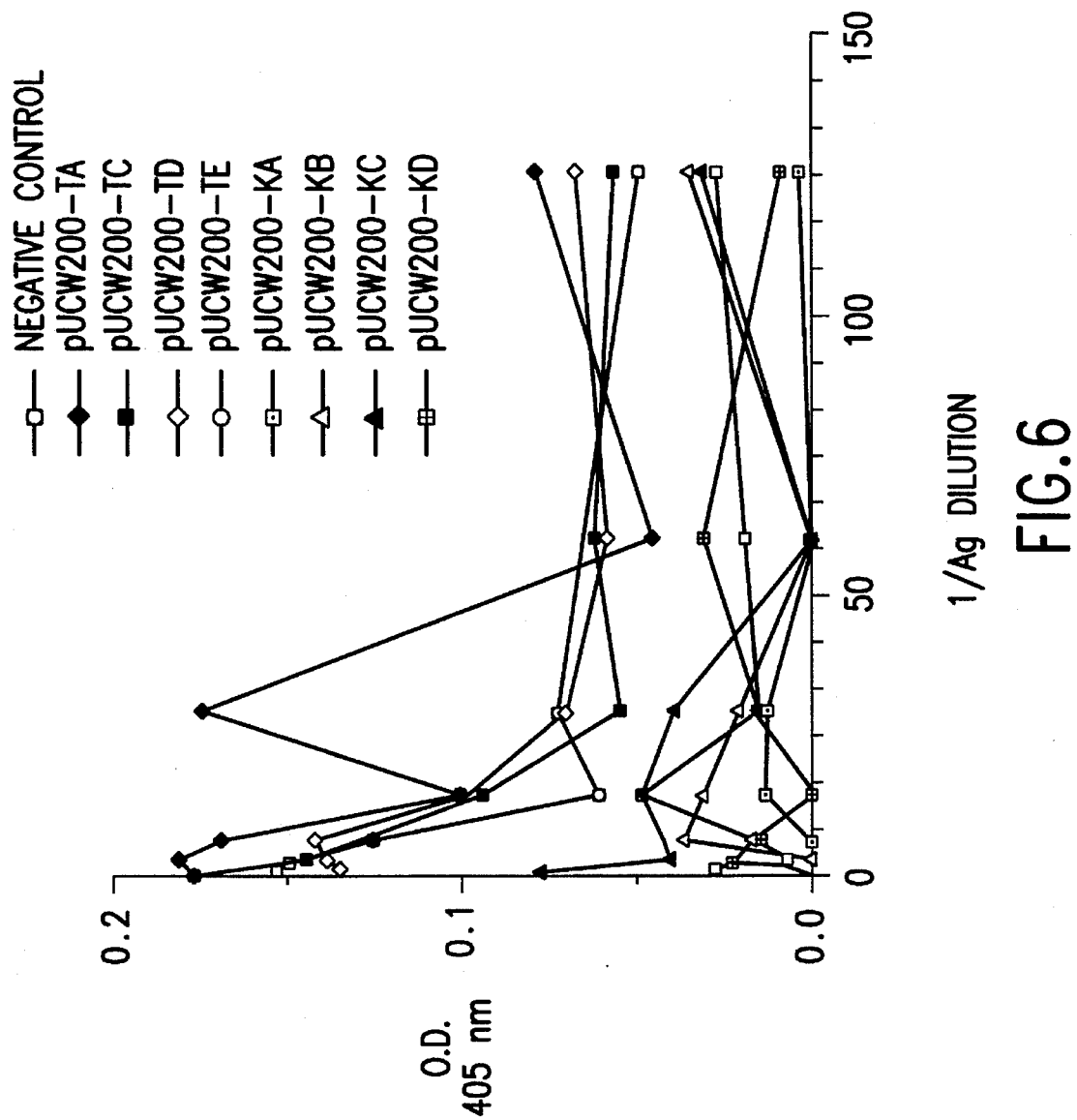
FIG. 6. ELISA of sweetgum 2027 selected on 2,4-D or kanamycin.

The transformation frequencies of pUCW200 isolates selected on 2,4-D were compared to those selected on kanamycin. ELISA for NPT-II was used as a measure of transformation frequency. Four isolates selected on 2,4-D and four isolates selected on kanamycin were assayed. The results are shown in FIG. 6. All four of the 2,4-D selected clones (designated 2027 (pUCW200)-TA, -TC, -TD and -TE) were positive for NPT-II, indicating that they are transformed. However, none of the kanamycin selected clones (designated 2027 (pUCW200)-KA, -KB, -KC, and -KD) were positive.

Plasmid pUCW200 differs from plasmid pBI121 in that pUCW200 has the 2,4-D resistance gene substituted for the GUS gene of pBI121. Since the transformation experiments using pBI121 with selection on kanamycin gave a transformation frequency of 6.5%, it is not surprising that none of the four kanamycin selected isolates assayed in this experiment were positive. However, these results establish the transformation frequency of pUCW200 into sweetgum, with selection on 2,4-D, at 100%. It is clear that this selection method is much better than the standard kanamycin selection.

The fact that 2,4-D selection did not yield any false positive isolates demonstrates that it is an outstanding selectable marker. Also, experiments have shown that sweetgum leaf pieces placed on 2,4-D containing media do not regenerate adventitious shoots. Since co-cultivated leaf pieces did regenerate adventitious shoots in the presence of 2,4-D and 100% of those shoots were transformed, these shoots must be using the 2,4-D resistance gene product to convert the 2,4-D in the media to 2,4-dichlorophenol. This indicates that these isolates are expressing the resistance gene.

Example 9

Description of Propagation Method.

Sweetgum were propagated by growing the adventitious shoots on WPM containing 0.01 mg/L NAA and 2.0 mg/L BA. The original shoot formed new shoots on this media. The new shoots were aseptically excised from the original shoot and grown independently. This propagation was repeated until the required number of shoots were generated. These shoots were then elongated by incubating them on WPM containing 0.5 mg/L BA. Elongated shoots of greater than 1 cm in length were then incubated on root induction media consisting of ⅓ strength WPM containing 0.1 mg/L IBA (indole-3-butyric acid). When roots began to form, the plantlets were transferred to plug trays containing a soilless mix consisting of equal parts peat, perlite, and vermiculite and incubated in 100% relative humidity until new growth appeared. The plantlets were then transplanted to 10 cubic inch leach tubes and grown in a greenhouse until they reach planting size. The plants are then hardened off to outdoor conditions until dormant, removed from tubes, and planted at the prepared site. At a specified time before and/or after planting, the site is sprayed with 2,4-D. The time for spraying the site and the concentration of 2,4-D used are readily determined by one skilled in the art. More specifically, these factors are determined by the growth of plants other than the transformed plants at the site. The amount of 2,4-D sprayed on the site is an amount sufficient to 1) inhibit the growth of non-transformed plants at the site and 2) allow the transformed plants to grow.

Example 10

Transformation and Propagation of Potato.

Potatoes (preferably, Russet Burbank potatoes) transformed with the tfdA gene are produced essentially as described by De Block, *Theor. Appl. Genet.* 76:767–774 (1988) except that 1) the regeneration media includes 0.1 mg/L 2,4-D and 2) kanamycin is not used in experiments with the tfdA gene.

Briefly, the procedure described by De Block, supra, is as follows:

Plant materials

Sterile plants of cvs 'Bintje', 'Desiree', 'Berolina' or 'Russet Burbank' are propagated in vitro by transferring the top shoots or 1-cm-long pieces of stem explants together with an auxiliary bud to S1 medium. The shoots are grown at 23° C. with a daylength of 16 h under 3000 lux light intensity (a mixture of "lumilux white" and "natura" from Osram, FRG).

Media

S1: B5 medium (Gamborg et al., *Exp. Cell. Res.* 50:151–158 (1968)) with 20 g/l sucrose and supplemented with 150 mg/l $CaCl_2.2H_2O$, 0.4% agarose, pH 5.8.

S2: MS medium (Murashige and Skoog, *Physiol. Plant* 15:473–479 (1962)) with 30 g/l sucrose and supplemented with 0.5 g/l MES pH 5.5, 20 g/l mannitol.

S3: MS medium without sucrose and supplemented with 200 mg/l glutamine, 0.5 g/l MES pH 5.7, 0.5 g/l PVP, 20 g/l mannitol, 20 g/l glucose, 40 mg/l adenine-$SO_4$, 0.5% agarose, 1 mg/l trans-zeatin, 0.1 mg/l NAA, 1 g/l carbenicillin or 0.5 g/l cefotaxime.

S4: S3 supplemented with 10 mg/l $AgNO_3$.

S5: S3 medium without NAA and an one-half concentration of antibiotics.

S6: S5 supplemented with 10 mg/l $AgNO_3$.

S7: S5 supplemented with 0.01 mg/l GA3; 250 mg/l carbenicillin or 150 mg/l cefotaxime.

S8: S5 supplemented with 0.1 mg/l GA3 and 10 mg/l $AgNO_3$; 250 mg/l carbenicillin or 150 mg/l cefotaxime.

Antibiotics, hormones, and $AgNO_3$ were added after autoclaving. $Ag_2S_2O_3$ was added as 10 mg/l $AgNO_3$+117 mg/l $Na_2S_2O_3.5H_2O$. Min A medium is as described (Miller, J. H., Experiments in molecular genetics. Cold Spring Harbor Laboratory Press, Cold Spring Harbor, N.Y. (1972)).

Transformation, Selection and Regeneration

Leaves (3–10 mm) from 3- to 4-week-old shoots are cut at the base. The leaves are not further wounded. About 10 wounded leaves are floated upside down on 10 ml of infection medium S2 contained in a 9 cm Petri dish, 30 µl of *Agrobacterium tumefaciens* LBA4404 containing plasmid pUCW200, which had been grown in Luria broth medium to late log, is added. The plates are then incubated at low light intensity (500 lux). After 2 days, the leaves are washed with S2 medium containing 1 g/l carbenicillin or 0.5 g/l cefotaxime, patted dry on filter paper, and placed upside down on medium S3 containing 0.1 mg/l 2,4-D. The Petri dishes are sealed with tape that allows gas diffusion ("urgo pore" tape, Urgo, Chenove, France) and are incubated at high light intensity (3000 lux, a mixture of "lumilux white" and "natura" from Osram, FRG). After 1 week, the leaves are transferred to fresh medium. After 2 more weeks, many small calli are formed at the wounded edges of the leaves, and the leaves are transferred to selective medium S5 for 'Berolina', 'Bintje' and 'Desiree', and S6 for 'Russet Burbank'. After 2–3 more weeks, those leaves with calli are transferred to medium S7 for 'Berolina', 'Bintje' and 'Desiree', and S8 for 'Russet Burbank'. From this point on, 250-ml glass jars are used.

When using cefotaxime in the medium, it is important to transfer the leaves to fresh medium every 10 days. After 2 weeks, the first shoots (0.5 cm high) are isolated and transferred to rooting medium S1 containing 100 mg/l carbenicillin or cefotaxime. Normally, the shoots root in about 1 week. When they do not root after 2 weeks, a thin slice is cut away from the stem base: most of these recut shoots root after 1 week. All shoots are harvested within a period of 3 weeks. In order to avoid isolating identical shoots, two shoots from the same or closely linked calli are never taken.

When roots began to form, the plantlets are transferred to plug trays containing a soilless mix consisting of equal parts peat, perlite, and vermiculite and incubated in 100% relative humidity until new growth appears. The plantlets are then transplanted to 10 cubic inch leach tubes and grown in a greenhouse until they reach planting size. The plants are then hardened off to outdoor conditions until dormant, removed from tubes, and planted at the prepared site. At a specified time before and/or after planting, the site is sprayed with 2,4-D. The time for spraying the site and the concentration of 2,4-D used are readily determined by one skilled in the art. More specifically, these factors are determined by the growth of plants other than the transformed plants at the site. The amount of 2,4-D sprayed on the site is an amount sufficient to 1) inhibit the growth of non-transformed plants at the site and 2) allow the transformed plants to grow.

Example 11

Transformation and Propagation of Soybean.

Soybeans (preferably, Winchester soybeans) transformed with the tfdA gene are produced essentially as described by Hinchee et al., *Bio/Technology* 6:917–921 (1988) except that 1) the regeneration media includes 0.1 mg/l 2,4-D and 2) kanamycin is not used in experiments with the tfdA gene.

Briefly, the procedure described by Hinchee et al., supra, is as follows:

Regeneration. Soybean (*Glycine max* (L.) Winchester) seedlings are aseptically germinated 4–10 days on 0.8% Difco purified agar at 25° C. under a photoperiod of 16:8 (cool white fluorescent light at 40 µEn/s). After washing in soapy water, rinsing in distilled water, and placing in 70% ethanol for 2 min; seeds are transferred to 50% Chlorox for 10–13 minutes followed by rinsing 5 times with sterile distilled water. Seeds are soaked in an aqueous Captan solution for 1 hour before transfer to the germination medium. After germination, cotyledons are removed and placed adaxial side down on $B_5BA$ medium. $B_5BA$ medium is composed of $B_5$ salts (Gamborg et al., *Exp. Cell Res.* 50:152–158 (1968)), 20 mg/l sucrose, 1.15 mg/l benzyladenine (BA), 0.1 mg/l 2,4-D, and 8 g/l Difco purified agar, at pH 5.8 prior to autoclaving. Cotyledon explants are transferred to $B_5O$ medium (identical to $B_5BA$ but without the BA) after 3–4 weeks. These and all other cultured explants are maintained under the same environmental conditions as the germinating seedlings. Cotyledon explants producing shoots are subcultured every 4 weeks onto fresh $B_5O$ medium. Elongating shoots are removed and placed on $½B_5O$ medium (half the major and minor salts of $B_5O$ medium) in capped glass vials or in sterile 50 ml disposable plastic centrifuge tubes. Plantlets (rooted shoots) are moved to vermiculite in 2" pots after several new leaves are produced. These plantlets are then placed in a plastic container which the lid is gradually opened to harden them off prior to growing in the greenhouse. Plantlets that produce new leaves after hardening off are transplanted into soil and grown in the greenhouse for flowering and seed set.

Cultivar screen. Soybean seeds are aseptically germinated for 5 days on 0.8% Difco purified agar. Hypocotyls are cut into 5 mm segments, and inoculated (Horsch et al., *Science* 227:1229–1231 (1985)) with *A. tumefaciens* LBA4404 containing plasmid pUCW200. The hypocotyl segments are co-cultured with Agrobacterium for 2 days on ⅒ SH medium (⅒ the major and minor salts of SH (Schenk and Hildebrandt, *Can. J. Bot.* 50:199–204 (1972))) prior to being placed on MS NAA/K medium containing 500 mg/l carbenicillin with or without 100 mg/l kanamycin. MS NAA/K medium is composed of MS salts and organics (Murashige and Skoog, *Physiol. Plant.* 15:473–497 (1962)) with 2.15 mg/l kinetin and 4.68 mg/l napthalene acetic acid (NAA). Each cultivar sample is represented by 20–40 segments. The hypocotyl segments remain on MS NAA/K for 4 weeks prior to scoring. The number of hypocotyls which produced callus is counted as well as the number of independent calli per explant.

Cotyledon explant transformation. Cotyledon explants of soybean cultivar Winchester are prepared as for regeneration. Transformation with *A. tumefaciens* LBA 4404 containing plasmid pUCW200 is carried out as described for the hypocotyls in the cultivar screen. Inoculated cotyledons are cultured as described for cotyledon regeneration, except that the $B_5BA$ medium contained 500 mg/l carbenicillin and 100 mg/l cefotaxime. Elongated shoots are cultured in $B_5O$ medium.

When roots began to form, the plantlets are transferred to plug trays containing a soilless mix consisting of equal parts peat, perlite, and vermiculite and incubated in 100% relative humidity until new growth appears. The plantlets are then transplanted to 10 cubic inch leach tubes and grown in a greenhouse until they reach planting size. The plants are then hardened off to outdoor conditions until dormant, removed from tubes, and planted at the prepared site. At a specified time before and/or after planting, the site is sprayed with 2,4-D. The time for spraying the site and the concentration of 2,4-D used are readily determined by one skilled in the art. More specifically, these factors are determined by the growth of plants other than the transformed plants at the site. The amount of 2,4-D sprayed on the site is an amount sufficient to 1) inhibit the growth of non-transformed plants at the site and 2) allow the transformed plants to grow.

All publications mentioned hereinabove are hereby incorporated by reference in their entirety.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of selecting for a transformed plant cell comprising:

a) transforming one or more plant cells with a polynucleotide comprising a tfdA gene expressible in said plant cell, and b) directly selecting on a culture medium the resulting transformed plant cell with an amount of 2,4-dichlorophenoxyacetic acid as a selectable agent, the 2,4-dichlorophenoxyacetic acid being in an amount which inhibits adventitious shoot regeneration of non-transformed plant cells, wherein adventitious shoot regeneration from said transformed plant cell is not inhibited.

2. The method according to claim 1, wherein said plant cell is a dicotyledonous plant cell.

3. The method according to claim 2, wherein said dicotyledonous plant cell is a hardwood plant cell.

4. The method according to claim 3, wherein said hardwood plant cell is a sweetgum plant cell.

5. The method according to claim 1, wherein said polynucleotide further comprises at least one second gene coding for a protein.

6. A method of selecting for a transformed plant comprising:

a) transforming one or more plant cells with a polynucleotide comprising a tfdA gene expressible in said plant cell, b) directly selecting on a culture medium the resulting transformed plant cell with an amount of 2,4-dichlorophenoxyacetic acid as a selectable agent, the 2,4-dichlorophenoxyacetic acid being in an amount which inhibits adventitious shoot regeneration of non-transformed plant cells, wherein adventitious shoot regeneration from said transformed plant cell is not inhibited, and c) regenerating the selected plant cell into a plant.

7. The method according to claim 6, wherein said plant is a dicotyledonous plant.

8. The method according to claim 7, wherein said dicotyledonous plant is a hardwood.

9. The method according to claim 8, wherein said hardwood is a sweetgum.

10. The method according to claim 6, wherein said polynucleotide further comprises at least one second gene coding for a protein.

11. A plant cell comprising a tfdA gene expressible in said plant cell wherein said plant cell is free of other foreign selectable marker genes.

12. The plant cell according to claim 11, wherein said plant cell is a dicotyledonous plant cell.

13. The plant cell according to claim 12, wherein said dicotyledonous plant cell is a hardwood plant cell.

14. The plant cell according to claim 13, wherein said hardwood plant cell is a sweetgum plant cell.

15. A plant regenerated from the plant cell according to claim 11.

16. Progeny of the plant according to claim 15, wherein said progeny comprises said tfdA gene.

17. A propagule of the plant according to claim 15, wherein said propagule comprises said tfdA gene.

18. A seed produced by the progeny according to claim 16, wherein said seed comprises said tfdA gene.

19. A sweetgum plant cell comprising a tfdA gene expressible in said plant cell.

20. A plant regenerated from the sweetgum plant cell according to claim 19.

21. Progeny of the plant according to claim 20, wherein said progeny comprises said tfdA gene.

22. A propagule of the plant according to claim 20, wherein said propagule comprises said tfdA gene.

23. A seed produced by the progeny according to claim 21, wherein said seed comprises said tfdA gene.

24. A method of producing a hardwood plantation comprising:
    a) transforming one or more plant cells with a polynucleotide comprising a tfdA gene expressible in said plant cell;
    b) regenerating said plant cell into a plant;
    c) culturing said regenerated plant with an amount of 2,4-dichlorophenoxyacetic acid which will kill non-transformed plants;
    d) selecting a plant exhibiting growth;
    e) propagating said plant to produce many plants;
    f) inducing root formation in said plants;
    g) growing said rooted plants to planting stock size;
    h) planting the planting stock size plants in a sheared, defoliated site, and
    i) applying 2,4-dichlorophenoxyacetic acid over the entire site to suppress competition growth until the planting stock can thrive without competition growth control.

25. A method of producing a hardwood plantation comprising:
    a) transforming one or more plant cells with a polynucleotide comprising a tfdA gene and at least one second gene encoding a foreign selectable marker expressible in said plant cell;
    b) culturing said plant cell with an amount of a chemical which will inhibit adventitious shoot regeneration of plant cells not transformed with the foreign selectable marker gene;
    c) selecting a plant cell exhibiting adventitious shoot regeneration;
    d) regenerating said plant cell into a plant;
    e) propagating said plant to produce many plants;
    f) inducing root formation in said plants;
    g) growing said rooted plants to planting stock size;
    h) planting the planting stock size plants in a sheared, defoliated site, and
    i) applying 2,4-dichlorophenoxyacetic acid over the entire site to suppress competition growth until the planting stock can thrive without competition growth control.

26. A method for producing a hardwood plantation comprising:
    a) transforming one or more plant cells with a polynucleotide comprising a tfdA gene and at least one second gene encoding a foreign selectable marker expressible in said plant cell;
    b) culturing said plant cell with an amount of a chemical which will inhibit adventitious shoot regeneration of plant cells not transformed with the foreign selectable marker gene;
    c) selecting a plant cell exhibiting adventitious shoot regeneration;
    d) regenerating said plant cell into a plant;
    e) culturing said regenerated plant with an amount of 2,4-dichlorophenoxyacetic acid which will kill non-transformed plants;
    f) selecting a plant exhibiting growth;
    g) propagating said plant to produce many plants;
    h) inducing root formation in said plants;
    i) growing said rooted plants to planting stock size;
    j) planting the planting stock size plants in a sheared, defoliated site, and
    k) applying 2,4-dichlorophenoxyacetic acid over the entire site to suppress competition growth until the planting stock can thrive without competition growth control.

27. The method of claim 26 wherein the hardwood is sweetgum.

28. The method of any one of claims 24–26, further comprising the step of adding nutrients to the site.

29. The method of any one of claims 24–26, further comprising the step of raking the site prior to planting the planting stock.

30. A method of producing a hardwood plantation comprising:
    planting stock size plants in a sheared, defoliated site, and
    applying 2,4-dichlorophenoxyacetic acid over the entire site to suppress competition growth until the planting stock can thrive without competition growth control, wherein said plant is a hardwood comprising a tfdA gene.

31. The method of claim 30, wherein the hardwood is sweetgum.

32. A plantation of hardwood trees comprising hardwood trees comprising a tfdA gene.

33. The plantation of claim 32, wherein the hardwood trees are sweetgum.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 2058 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 751..1611

( x i ) SEQUENCE DESCRIPTION: SEQ ID NO:1:

```
GGATCCTGTC  TCAGCTGGCG  CGCAATGCTC  GAACCCGCTG  CGATATACAG  CCGTTCGTAG        60

TGCAGGTGCT  CCACCGTGAT  TCCAGGCTCC  TGGGGGTAGA  AGCGGCCGAC  ACCGAGATGG       120

ATGGTGCCGG  CACGCAGGGC  CTCGATCTGC  CGCACCTTGG  GCATCAGGGC  CAGAGACAGC       180

GTCGCCCCCG  GGACCGCCTG  CGTGAACGCA  TGGAGCAATG  CCGGGACGGT  CTGGTAGATC       240

GCCGTGCCGA  GGTAGCCGAT  ATCGAGTTGG  CCGATCTCGC  CCCGGCTGGC  GGCGCGGGAC       300

CGGTCCACGG  AAGTCCGACC  CAGTTCGAGC  ATGCGCCGTG  CATCTTCGAG  AAACGCGGCC       360

CCGGCGGGCG  TGAGCTGCAC  GCCGCGCGCG  CTGCGCTCGA  ACAACAACAC  GCCCAGATGC       420

TGTTCGAGCG  CGTGAATCTG  TCGCGTGACC  GGGGGCTGGG  AAATATGCAG  CCGCCGCGCG       480

GCGGCACCGA  CGTTGCCCTC  CTCCGCGGCA  GCAACGAAAT  AGCGAAGCTG  TCGAAACTCC       540

ATTCTTCACT  CCTGGTGGCT  GGCTCCGGCT  GCCGGAGAGC  CATACCGATC  CCGTATCGCT       600

CGCGCTGATG  GAAGGTATTA  GACCATATGG  CCCGGCATTT  CTAGACTACC  GCCATGATAA       660

AACTCGGCTG  CTCTCTCGTC  TGCTGGAACA  TCTTCAGGCG  CGCTGAGCCG  TCTTTTTGAA       720
```

ACAGTCTCTT AGAAAGGAG CAAAAAGTG AGC GTC GTC GCA AAT CCC CTT CAT     774
                               Ser Val Val Ala Asn Pro Leu His
                                1                5

CCT CTT TTC GCC GCA GGG GTC GAA GAC ATC GAC CTT CGA GAG GCC TTG     822
Pro Leu Phe Ala Ala Gly Val Glu Asp Ile Asp Leu Arg Glu Ala Leu
    10              15                  20

GGT TCG ACC GAG GTC CGA GAG ATC GAA CGG CTA ATG GAC GAG AAG TCG     870
Gly Ser Thr Glu Val Arg Glu Ile Glu Arg Leu Met Asp Glu Lys Ser
 25              30                  35                  40

GTG CTG GTG TTC CGG GGG CAG CCC CTG AGT CAG GAT CAG CAG ATC GCC     918
Val Leu Val Phe Arg Gly Gln Pro Leu Ser Gln Asp Gln Gln Ile Ala
                45                  50                  55

TTC GCG CGC AAT TTC GGG CCA CTC GAA GGC GGT TTC ATC AAG GTC AAT     966
Phe Ala Arg Asn Phe Gly Pro Leu Glu Gly Gly Phe Ile Lys Val Asn
            60                  65                  70

CAA AGA CCT TCG AGA TTC AAG TAC GCG GAG TTG GCG GAC ATC TCG AAC    1014
Gln Arg Pro Ser Arg Phe Lys Tyr Ala Glu Leu Ala Asp Ile Ser Asn
        75                  80                  85

GTC AGT CTC GAC GGC AAG GTC GCG CAA CGC GAT GCG CGC GAG GTG GTC    1062
Val Ser Leu Asp Gly Lys Val Ala Gln Arg Asp Ala Arg Glu Val Val
    90                  95                 100

| | | | | | | | | | | | | | | | | |
|---|---|---|---|---|---|---|---|---|---|---|---|---|---|---|---|---|
| GGG | AAC | TTC | GCG | AAC | CAG | CTC | TGG | CAC | AGC | GAC | AGC | TCC | TTT | CAG | CAA | 1110 |
| Gly | Asn | Phe | Ala | Asn | Gln | Leu | Trp | His | Ser | Asp | Ser | Ser | Phe | Gln | Gln | |
| 105 | | | | 110 | | | | 115 | | | | | | 120 | | |
| CCT | GCT | GCC | CGC | TAC | TCG | ATG | CTC | TCC | GCG | GTG | GTG | GTT | CCG | CCG | TCG | 1158 |
| Pro | Ala | Ala | Arg | Tyr | Ser | Met | Leu | Ser | Ala | Val | Val | Val | Pro | Pro | Ser | |
| | | | | 125 | | | | | 130 | | | | | 135 | | |
| GGC | GGC | GAC | ACC | GAG | TTC | TGC | GAC | ATG | CGT | GCG | GCA | TAC | GAC | GCG | CTG | 1206 |
| Gly | Gly | Asp | Thr | Glu | Phe | Cys | Asp | Met | Arg | Ala | Ala | Tyr | Asp | Ala | Leu | |
| | | | 140 | | | | | 145 | | | | | 150 | | | |
| CCT | CGG | GAC | CTC | CAA | TCC | GAG | TTG | GAA | GGG | CTG | CGT | GCC | GAG | CAC | TAC | 1254 |
| Pro | Arg | Asp | Leu | Gln | Ser | Glu | Leu | Glu | Gly | Leu | Arg | Ala | Glu | His | Tyr | |
| | | | 155 | | | | 160 | | | | | 165 | | | | |
| GCA | CTG | AAC | TCC | CGC | TTC | CTG | CTC | GGC | GAC | ACC | GAC | TAT | TCG | GAA | GCG | 1302 |
| Ala | Leu | Asn | Ser | Arg | Phe | Leu | Leu | Gly | Asp | Thr | Asp | Tyr | Ser | Glu | Ala | |
| | 170 | | | | | 175 | | | | | 180 | | | | | |
| CAA | CGC | AAT | GCC | ATG | CCG | CCG | GTC | AAC | TGG | CCG | CTG | GTT | CGA | ACC | CAC | 1350 |
| Gln | Arg | Asn | Ala | Met | Pro | Pro | Val | Asn | Trp | Pro | Leu | Val | Arg | Thr | His | |
| 185 | | | | 190 | | | | | 195 | | | | | 200 | | |
| GCC | GGC | TCC | GGG | CGC | AAG | TTT | CTC | TTC | ATC | GGC | GCG | CAC | GCG | AGC | CAC | 1398 |
| Ala | Gly | Ser | Gly | Arg | Lys | Phe | Leu | Phe | Ile | Gly | Ala | His | Ala | Ser | His | |
| | | | | 205 | | | | | 210 | | | | | 215 | | |
| GTC | GAA | GGC | CTT | CCG | GTG | GCC | GAA | GGC | CGG | ATG | CTG | CTT | GCG | GAG | CTT | 1446 |
| Val | Glu | Gly | Leu | Pro | Val | Ala | Glu | Gly | Arg | Met | Leu | Leu | Ala | Glu | Leu | |
| | | | 220 | | | | | 225 | | | | | 230 | | | |
| CTC | GAG | CAC | GCG | ACA | CAG | CGG | GAA | TTC | GTG | TAC | CGG | CAT | CGC | TGG | AAC | 1494 |
| Leu | Glu | His | Ala | Thr | Gln | Arg | Glu | Phe | Val | Tyr | Arg | His | Arg | Trp | Asn | |
| | | 235 | | | | | 240 | | | | | 245 | | | | |
| GTG | GGA | GAT | CTG | GTG | ATG | TGG | GAC | AAC | CGC | TGC | GTT | CTT | CAC | CGC | GGA | 1542 |
| Val | Gly | Asp | Leu | Val | Met | Trp | Asp | Asn | Arg | Cys | Val | Leu | His | Arg | Gly | |
| | 250 | | | | | 255 | | | | | 260 | | | | | |
| CGC | AGG | TAC | GAC | ATC | TCG | GCC | AGG | CGT | GAG | CTG | CGC | CGG | GCG | ACC | ACC | 1590 |
| Arg | Arg | Tyr | Asp | Ile | Ser | Ala | Arg | Arg | Glu | Leu | Arg | Arg | Ala | Thr | Thr | |
| 265 | | | | 270 | | | | | 275 | | | | | 280 | | |
| CTG | GAC | GAT | GCC | GTC | GTC | TAGCGCACGC | CATGGCGCAC | GCCCTTTCG | | | | | | | | 1638 |
| Leu | Asp | Asp | Ala | Val | Val | | | | | | | | | | | |
| | | | | 285 | | | | | | | | | | | | |

| | | | | |
|---|---|---|---|---|
| CGAAGGCCCC | ACAAGATGTA | CGCAACCCTG | ATCAGCGGCA | GCCGTAGCCT | GGACGGCGAC | 1698 |
| ACCTTGGCGC | AGCGCGTCCT | TCGAGCGGCG | GGCGGCCTGG | CGGCATGGGG | ATTGAGGCCC | 1758 |
| GGTGATGTCG | TCGCCATCCT | CATGCGCAAT | GACTTTCCGG | TGCTCGAAAT | GACGCTGGCC | 1818 |
| GCGAACCGCG | CCGGCATCGT | TGCGGTGCCT | TTGAACTGGC | ATGCGAACCG | GGACGAGATC | 1878 |
| GCCTTCATCC | TCGAGGACTG | CAAAGCGCGT | GTGCTCGTCG | CGCACACCGA | TCTGCTCAAG | 1938 |
| GGCGTTGCAT | CCGCGGTGCC | CGAGGCCTGC | AAGGTGCTGG | AAGCCGCGTC | GCCGCCCGAG | 1998 |
| ATCCGGCAGG | CCTATCGGCT | GTCCGATGCG | TCGTGCACGG | CGAACCCGGG | CACGGTCGAC | 2058 |

( 2 ) INFORMATION FOR SEQ ID NO:2:

( i ) SEQUENCE CHARACTERISTICS:
        ( A ) LENGTH: 286 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Ser | Val | Val | Ala | Asn | Pro | Leu | His | Pro | Leu | Phe | Ala | Ala | Gly | Val | Glu |
| 1 | | | | 5 | | | | | 10 | | | | | 15 | |
| Asp | Ile | Asp | Leu | Arg | Glu | Ala | Leu | Gly | Ser | Thr | Glu | Val | Arg | Glu | Ile |
| | | | 20 | | | | | 25 | | | | | 30 | | |

```
Glu  Arg  Leu  Met  Asp  Glu  Lys  Ser  Val  Leu  Val  Phe  Arg  Gly  Gln  Pro
          35                       40                      45

Leu  Ser  Gln  Asp  Gln  Gln  Ile  Ala  Phe  Ala  Arg  Asn  Phe  Gly  Pro  Leu
     50                       55                      60

Glu  Gly  Gly  Phe  Ile  Lys  Val  Asn  Gln  Arg  Pro  Ser  Arg  Phe  Lys  Tyr
65                       70                      75                       80

Ala  Glu  Leu  Ala  Asp  Ile  Ser  Asn  Val  Ser  Leu  Asp  Gly  Lys  Val  Ala
               85                       90                      95

Gln  Arg  Asp  Ala  Arg  Glu  Val  Val  Gly  Asn  Phe  Ala  Asn  Gln  Leu  Trp
          100                      105                     110

His  Ser  Asp  Ser  Ser  Phe  Gln  Gln  Pro  Ala  Ala  Arg  Tyr  Ser  Met  Leu
          115                      120                     125

Ser  Ala  Val  Val  Val  Pro  Pro  Ser  Gly  Gly  Asp  Thr  Glu  Phe  Cys  Asp
     130                      135                     140

Met  Arg  Ala  Ala  Tyr  Asp  Ala  Leu  Pro  Arg  Asp  Leu  Gln  Ser  Glu  Leu
145                      150                     155                       160

Glu  Gly  Leu  Arg  Ala  Glu  His  Tyr  Ala  Leu  Asn  Ser  Arg  Phe  Leu  Leu
               165                      170                     175

Gly  Asp  Thr  Asp  Tyr  Ser  Glu  Ala  Gln  Arg  Asn  Ala  Met  Pro  Pro  Val
               180                      185                     190

Asn  Trp  Pro  Leu  Val  Arg  Thr  His  Ala  Gly  Ser  Gly  Arg  Lys  Phe  Leu
          195                      200                     205

Phe  Ile  Gly  Ala  His  Ala  Ser  His  Val  Glu  Gly  Leu  Pro  Val  Ala  Glu
     210                      215                     220

Gly  Arg  Met  Leu  Leu  Ala  Glu  Leu  Leu  Glu  His  Ala  Thr  Gln  Arg  Glu
225                           230                     235                  240

Phe  Val  Tyr  Arg  His  Arg  Trp  Asn  Val  Gly  Asp  Leu  Val  Met  Trp  Asp
               245                      250                     255

Asn  Arg  Cys  Val  Leu  His  Arg  Gly  Arg  Arg  Tyr  Asp  Ile  Ser  Ala  Arg
               260                      265                     270

Arg  Glu  Leu  Arg  Arg  Ala  Thr  Thr  Leu  Asp  Asp  Ala  Val  Val
          275                      280                     285
```